(12) United States Patent
Farina et al.

(10) Patent No.: US 9,360,400 B2
(45) Date of Patent: Jun. 7, 2016

(54) SAMPLING APPARATUS FOR DETERMINING THE AMOUNT AND UNIFORMITY OF A DELIVERED DOSE OF DRUG AND RELATED METHODS

(71) Applicant: Proveris Scientific Corporation, Marlborough, MA (US)

(72) Inventors: Dino J. Farina, Sudbury, MA (US); Timothy R. L'Ecuyer, Jefferson, MA (US); Spencer Pallas, Waltham, MA (US); Jason Graaf, Redding, CT (US)

(73) Assignee: Proveris Scientific Corporation, Marlborough, MA (US)

( * ) Notice: Subject to any disclaimer, the term of this patent is extended or adjusted under 35 U.S.C. 154(b) by 0 days.

(21) Appl. No.: 14/788,324

(22) Filed: Jun. 30, 2015

(65) Prior Publication Data

US 2015/0377749 A1    Dec. 31, 2015

Related U.S. Application Data

(60) Provisional application No. 62/019,228, filed on Jun. 30, 2014.

(51) Int. Cl.
*G01N 1/22* (2006.01)
*A61M 15/00* (2006.01)
*G01N 1/24* (2006.01)

(52) U.S. Cl.
CPC .......... *G01N 1/2205* (2013.01); *A61M 15/009* (2013.01); *A61M 15/00* (2013.01); *A61M 2202/064* (2013.01); *A61M 2206/14* (2013.01); *A61M 2209/02* (2013.01); *G01N 2001/2285* (2013.01); *G01N 2001/248* (2013.01)

(58) Field of Classification Search
CPC ................... G01N 1/2205; G01N 2201/2285; G01N 2001/248; A61M 15/009
See application file for complete search history.

(56) References Cited

U.S. PATENT DOCUMENTS

| | | | |
|---|---|---|---|
| 5,503,144 | A | 4/1996 | Bacon |
| 6,481,301 | B2 | 11/2002 | Pawliszyn |
| 7,686,016 | B2 | 3/2010 | Wharton et al. |

OTHER PUBLICATIONS

International Search Report and Written Opinion from International Application No. PCT/US2015/38658 dated Oct. 6, 2015.
Copley Scientific, Quality Solutions for Inhaler Testing; 2007, pp. 12-18 & 20; retrieved Aug. 31, 2015 <<https://www.copleyscientific.com>>.

*Primary Examiner* — Paul West
(74) *Attorney, Agent, or Firm* — Greenberg Traurig, LLP

(57) ABSTRACT

In an embodiment, the present invention is an apparatus, configured to collect emitted sample dose from a drug delivery device, wherein the sample dose is an aerosol, wherein the apparatus comprises a collection assembly and a removable plunger.

19 Claims, 22 Drawing Sheets

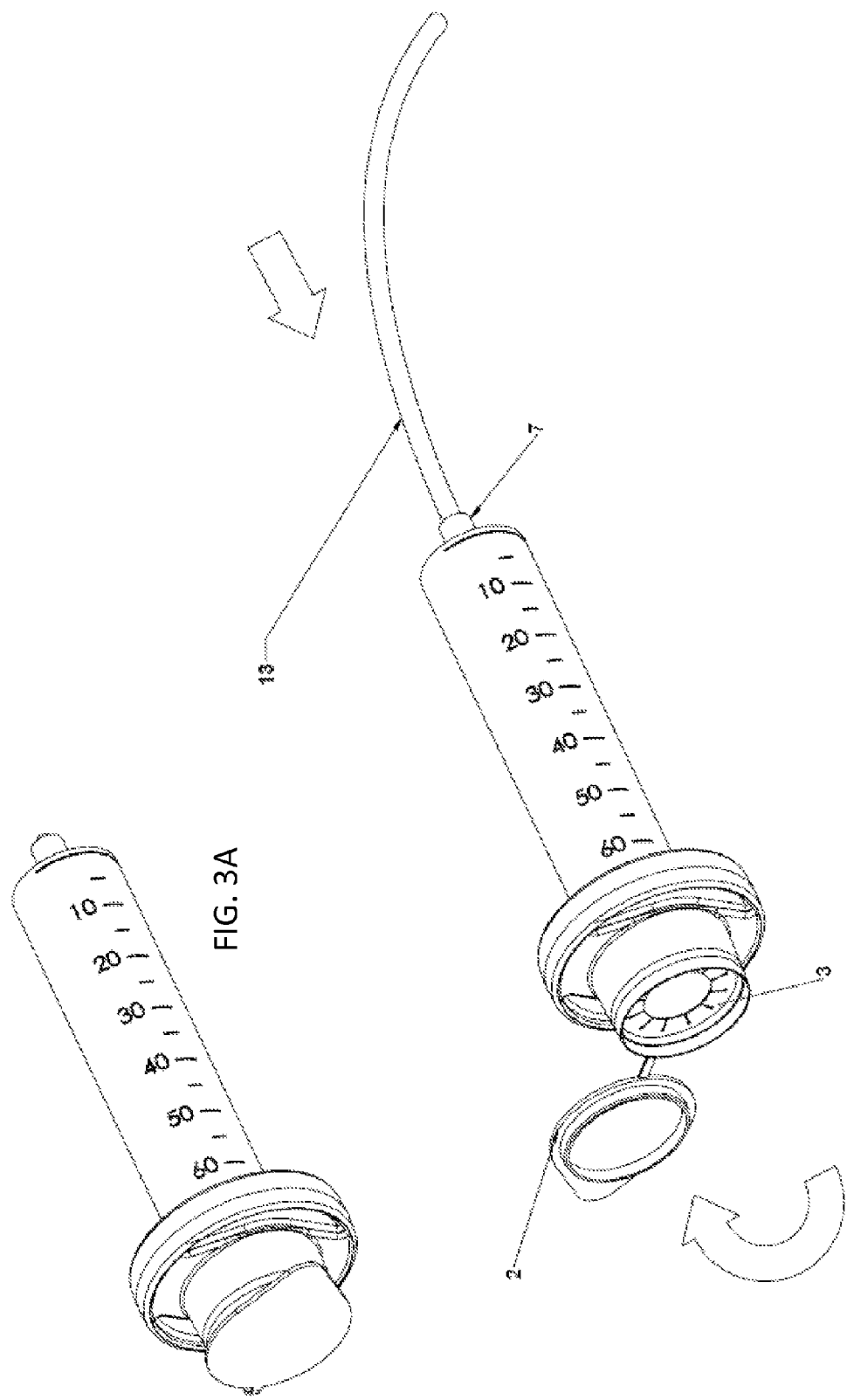

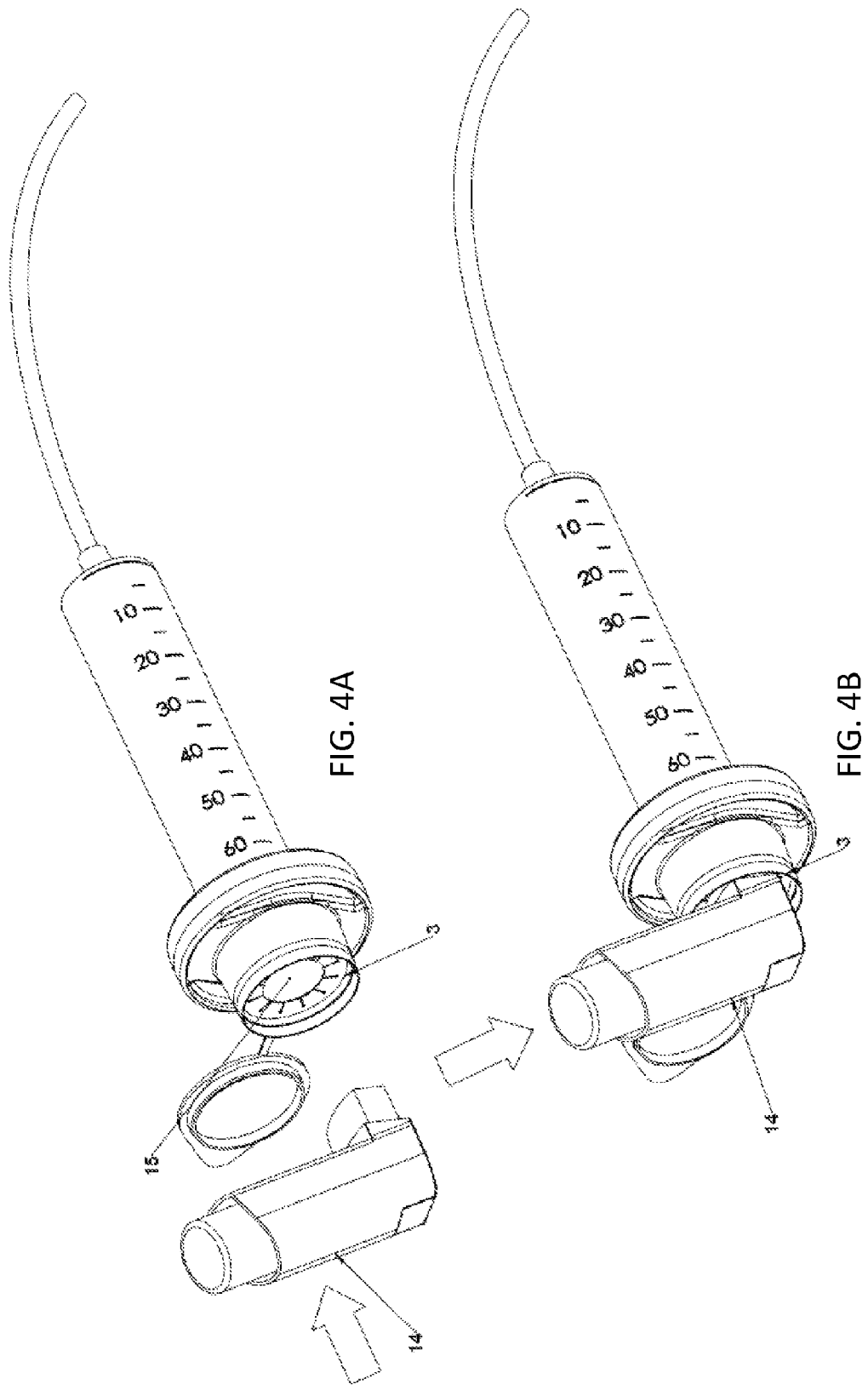

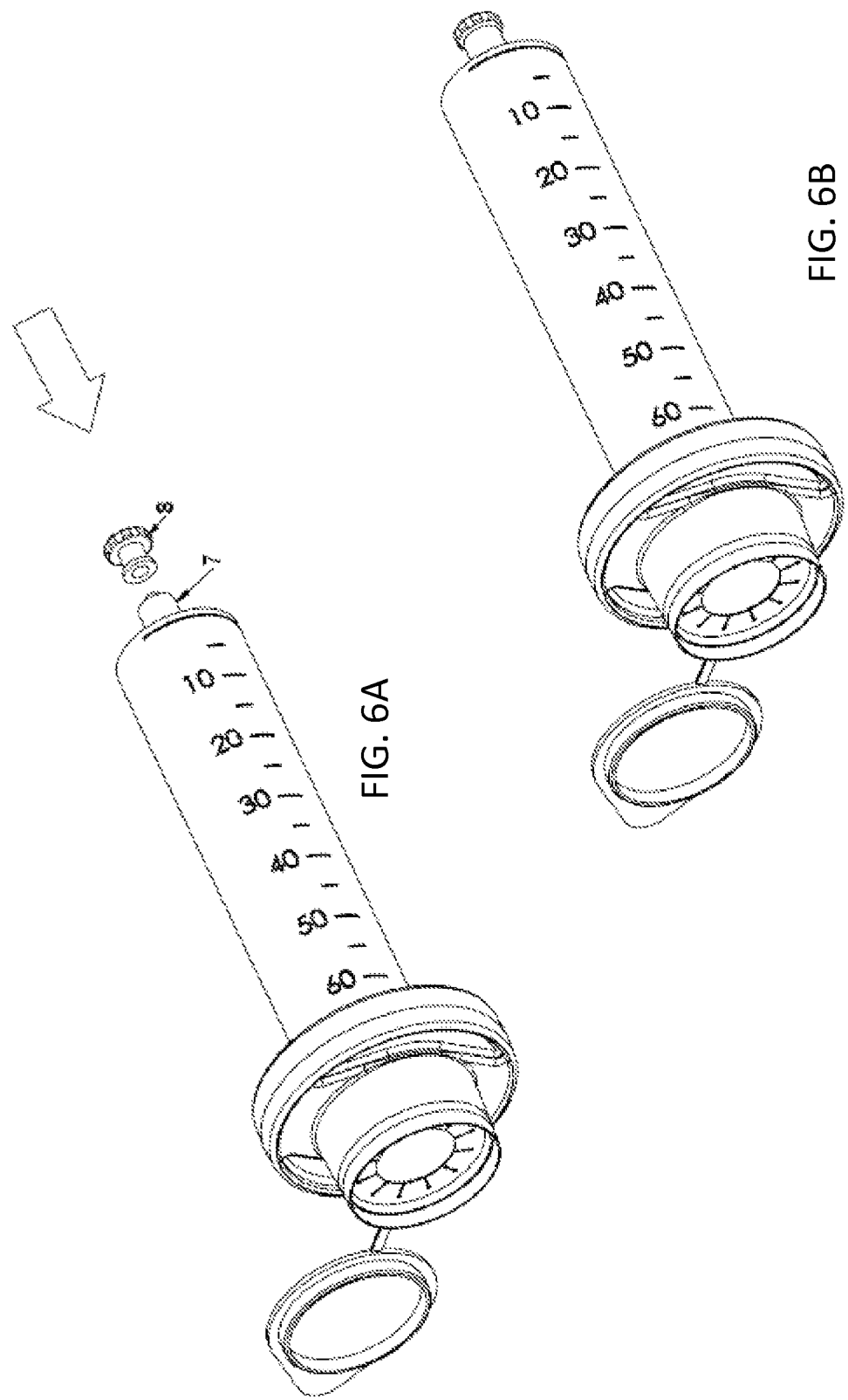

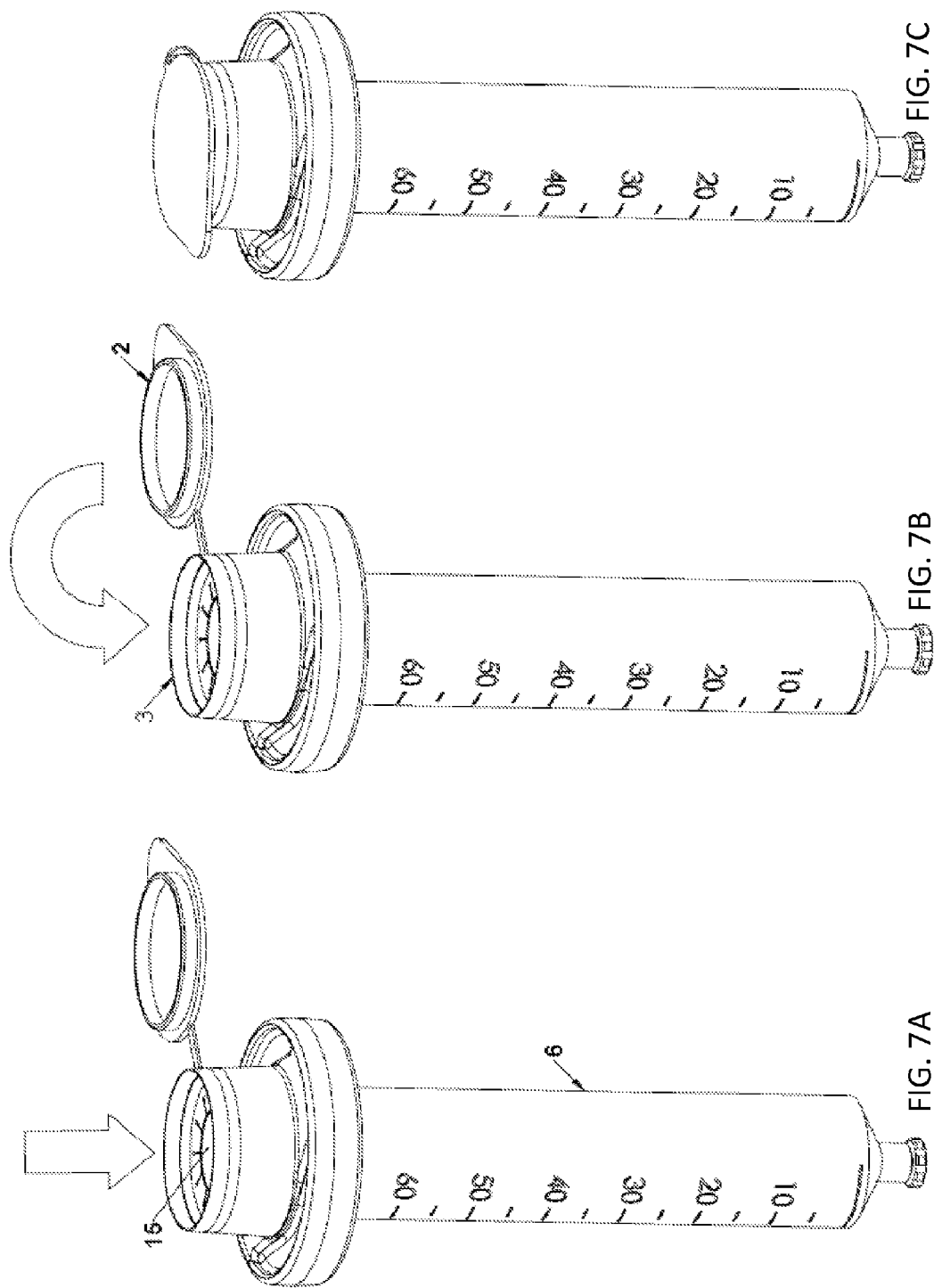

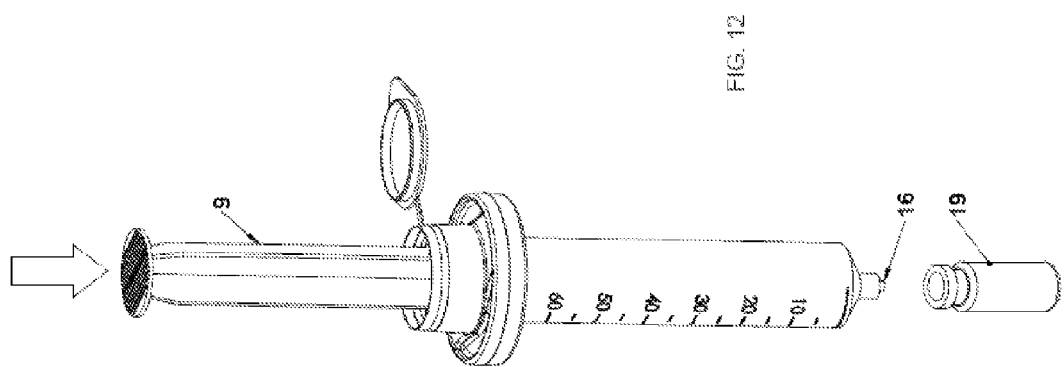

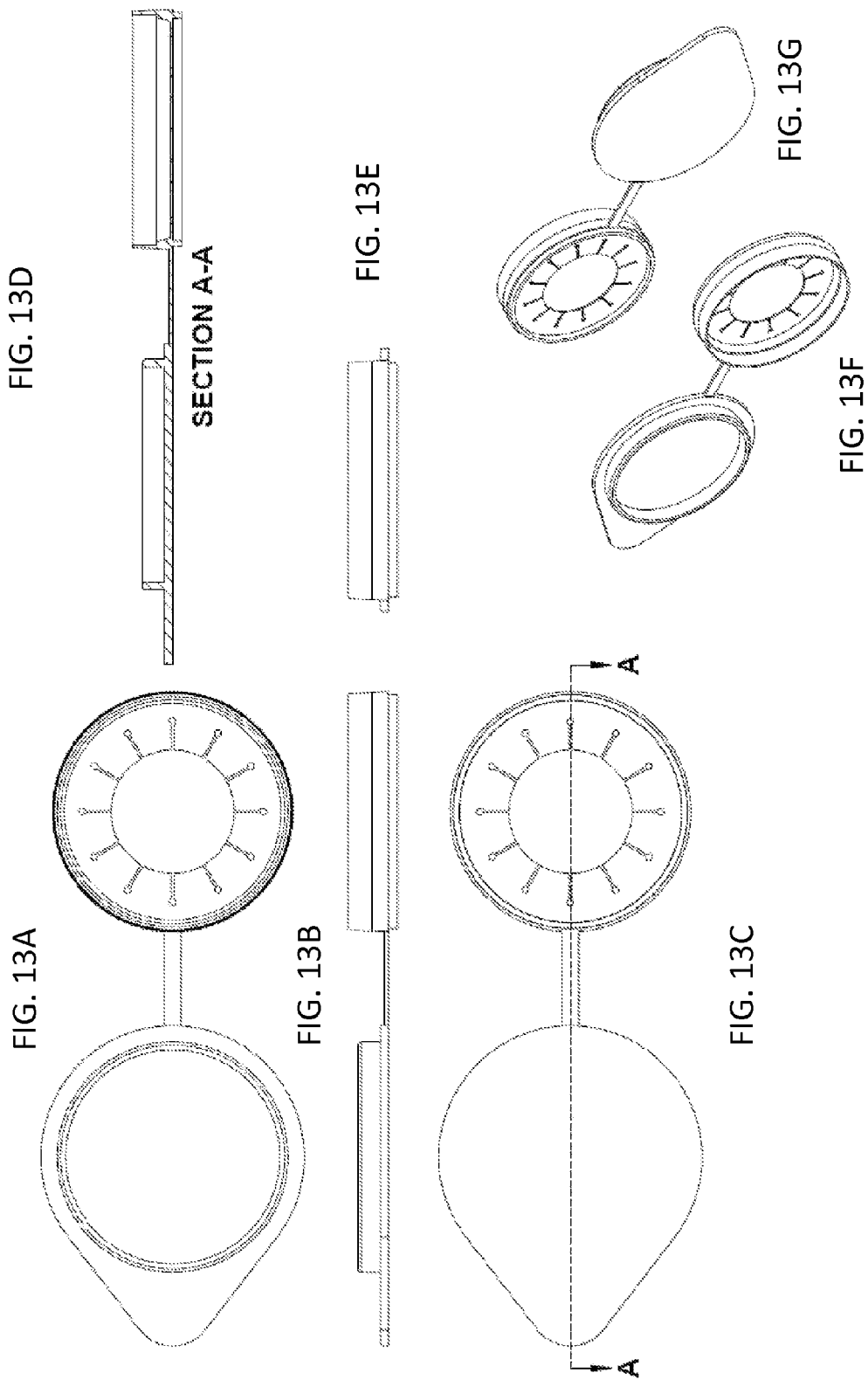

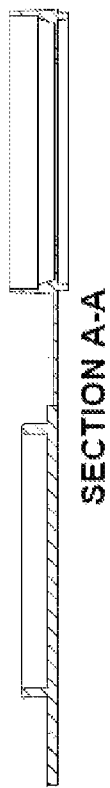
FIG. 14D
SECTION A-A
FIG. 14E
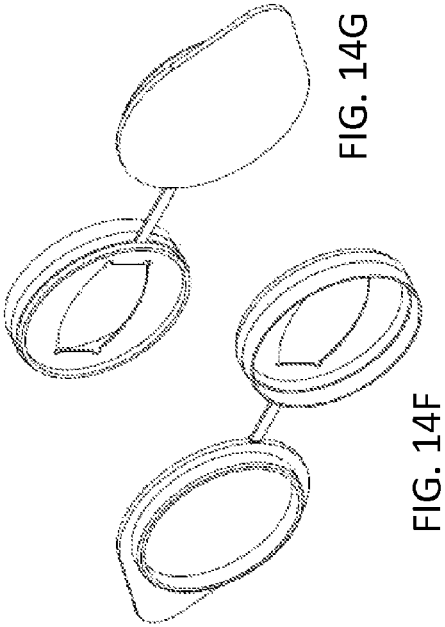
FIG. 14G
FIG. 14F
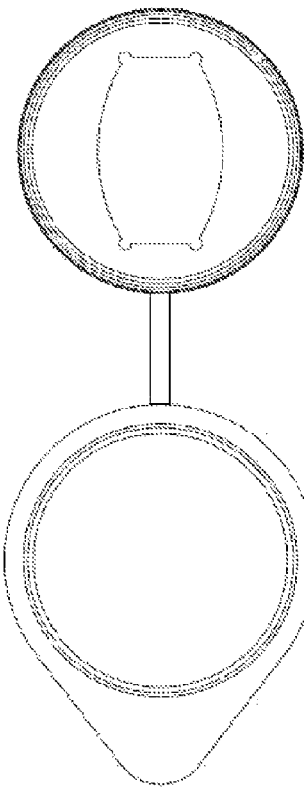
FIG. 14A
FIG. 14B
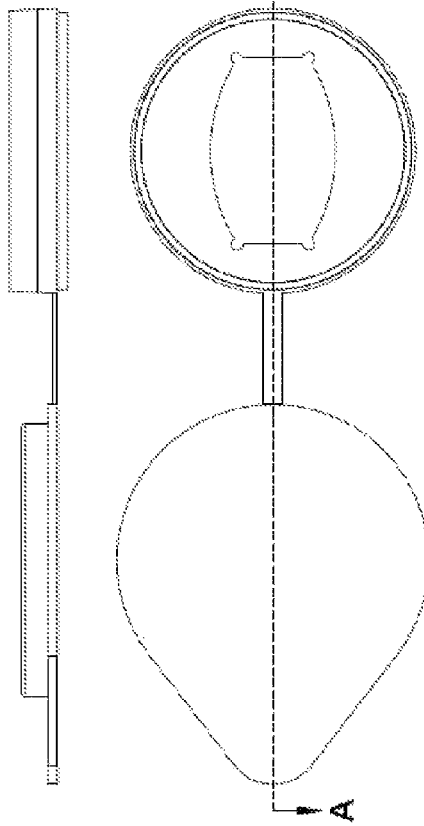
FIG. 14C

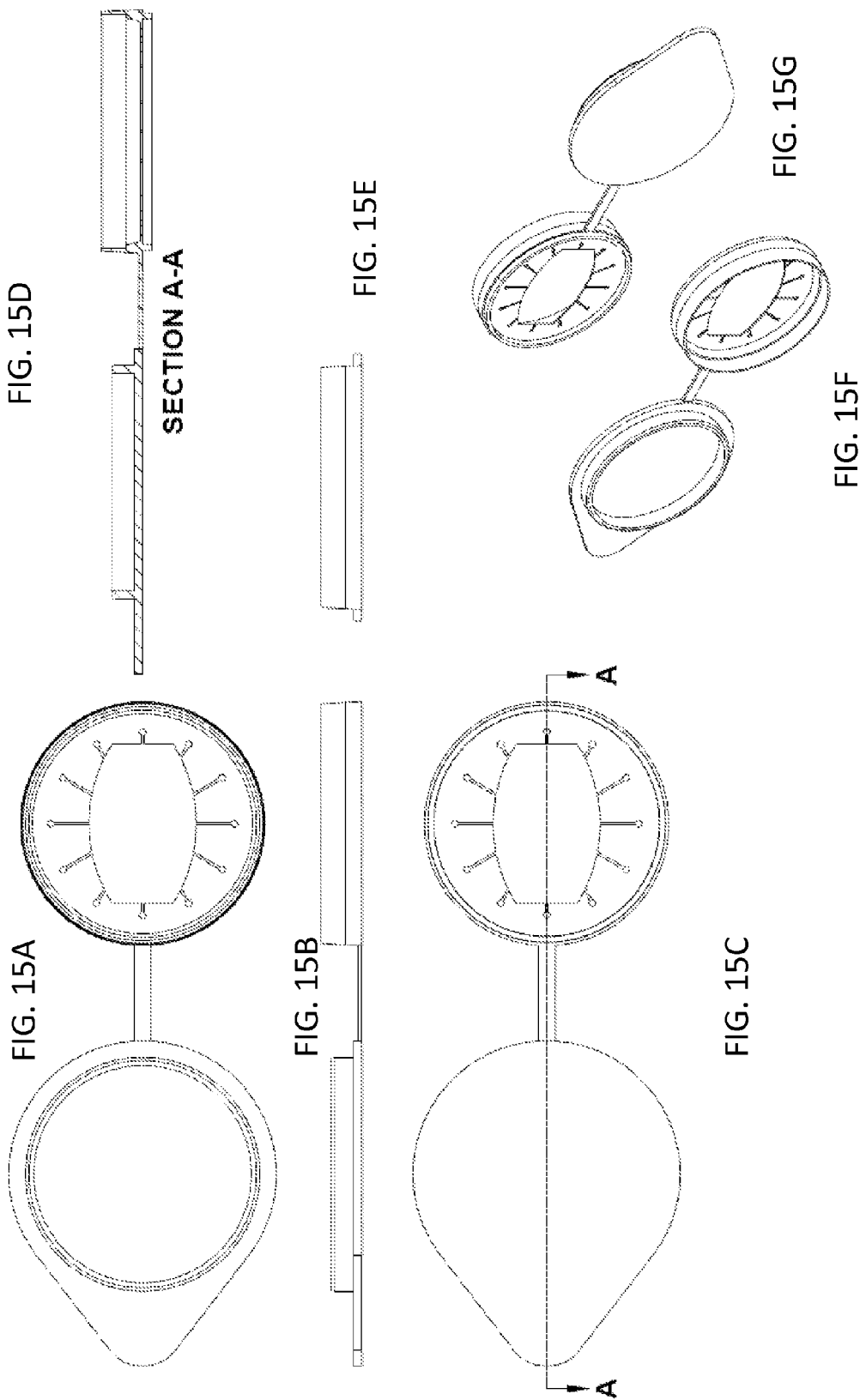

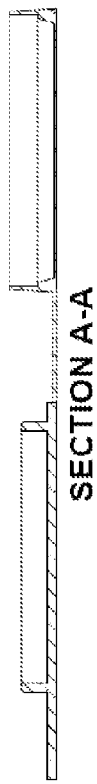
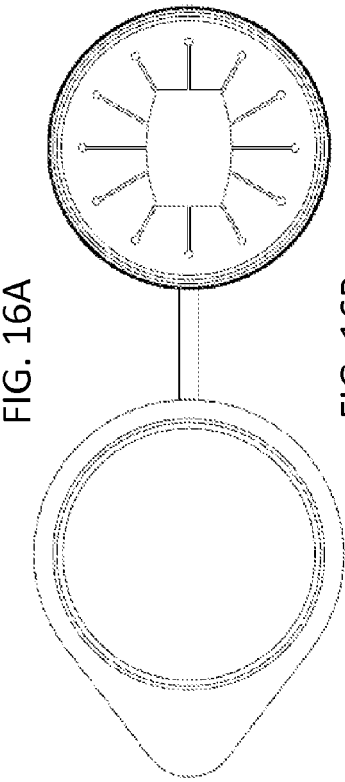
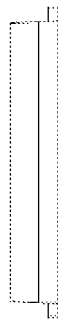
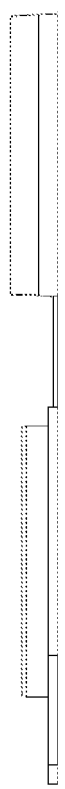
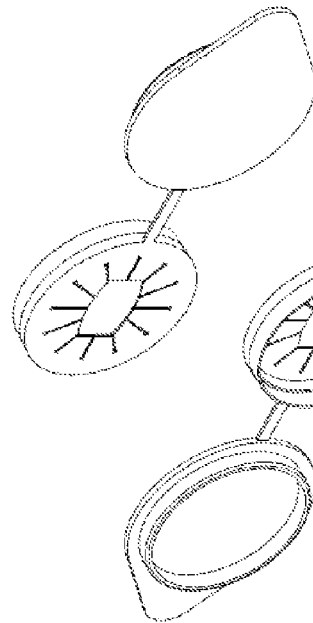
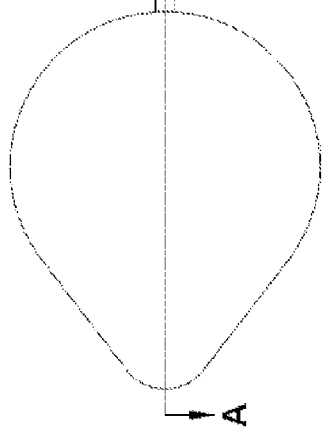

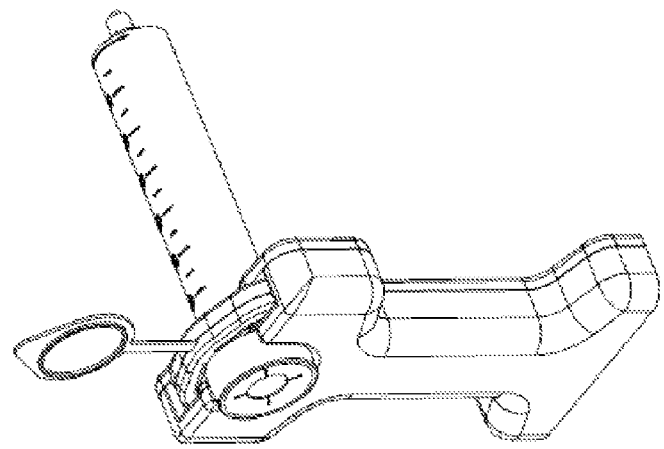
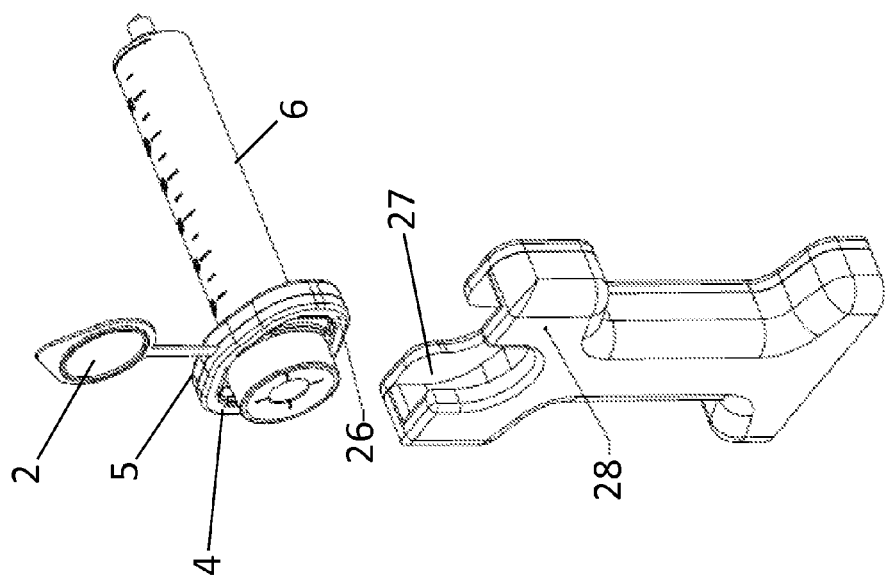
FIG. 22

SAMPLING APPARATUS FOR DETERMINING THE AMOUNT AND UNIFORMITY OF A DELIVERED DOSE OF DRUG AND RELATED METHODS

CROSS REFERENCE TO RELATED APPLICATIONS

This application claims priority to U.S. Provisional Patent Application No. 62/019,228, filed Jun. 30, 2014, the contents of which is hereby incorporated by reference in its entirety.

BACKGROUND

Developers of drugs delivered by means of a dry powder or aerosol spray perform certain tests of the drug formulation to ensure that the proper dose of the drug is delivered when a patient actuates the drug delivery device, such as a pressurized metered dose inhaler (pMDI) or a metered dose inhaler (MDI) or a dry powder inhaler (DPI). Traditional methods for collecting aerosol spray particles emitted when the drug delivery device is actuated—a sample dose—include multiple inefficiencies and risks for compromising the integrity of a sample dose.

SUMMARY

The present invention relates to a sampling apparatus for determining the amount and uniformity of a delivered dose of a drug and related methods for the collection of aerosol spray particles. In an embodiment, the present invention overcomes the inefficiencies and risks for compromising the integrity of a sample dose emitted from a drug delivery device that are present with the traditional test preparation methods, by allowing a user to use just one container to collect the sample dose and prepare the sample dose for testing. As a result, in an embodiment the present invention offers significant cost and time savings over traditional methods, while increasing the accuracy and repeatability of test results.

According to aspects illustrated herein, in an embodiment the present invention relates to a sampling apparatus that includes a collection container, a resealable inlet baffle, an inlet baffle cap, a filter, a resealable nozzle, a nozzle cap, and a plunger. In an embodiment, the resealable inlet baffle and the inlet baffle cap form a closure assembly. In an embodiment, the resealable inlet baffle and the inlet baffle cap are connected. In an embodiment, the collection container is a syringe that has an outer and an inner surface that are cylindrically shaped, a nozzle (the "nozzle end"), and a flange or flanges at the end of the syringe opposite to the nozzle (the "flange end"). The flange end of the syringe has the inlet baffle. In an embodiment, the flange end has two flat opposing, protruding flanges. In an embodiment, the flange end has a flat rim around the outer end circumference of the syringe opposite to the nozzle. For purposes of this invention, the term "mouthpiece" refers to the portion of a MDI or pMDI or DPI device that will enter a user's mouth during actuation of the device. In an embodiment of the invention, the inlet baffle is affixed to the collection container by means of an inlet ring and an inlet locking ring. In an embodiment of the invention, the inlet baffle screws on to the collection container. In an embodiment, the inlet baffle is held in place inside the inlet ring by a lead-in adaptor. In an embodiment the inlet baffle and the collection container are a single unit, formed from one piece of material.

According to aspects illustrated herein, in an embodiment the present invention relates to an inlet baffle comprising an opening, that when positioned on a sampling apparatus of the present invention, restrains the flow of spray particles out of the collection container from the end of the collection container in which a MDI or pMDI or DPI mouthpiece is inserted into the inlet baffle if a MDI or pMDI or DPI device is actuated into the collection container. In an embodiment, the inlet baffle is sufficiently sized and capable of being shaped to accept the mouthpiece of a MDI device. In an embodiment the inlet baffle is sufficiently sized and capable of being shaped to accept the mouthpiece of a pMDI device. In an embodiment the inlet baffle is sufficiently sized and capable of being shaped to accept the mouthpiece of a DPI device. In an embodiment, the inlet baffle is sufficiently sized and capable of being shaped to accept a plunger. In an embodiment of the invention, the inlet baffle is sufficiently sized and capable of being shaped to accept (i) the mouthpiece of a MDI device or a pMDI device or a DPI device, or (ii) the plunger once the MDI or pMDI or DPI device has been removed from the inlet baffle. In an embodiment of the invention, the inlet baffle is affixed to a collection container by means of an inlet ring and an inlet locking ring. In an embodiment of the invention, the inlet baffle screws on to the collection container. In an embodiment, the inlet baffle is held in place inside the inlet ring by a lead-in adaptor. In an embodiment the inlet baffle and the collection container are a single unit, formed from one piece of material. In an embodiment the inlet baffle has a cap to allow a user to cover the inlet baffle.

In an embodiment of the invention, the resealable nozzle has a threaded surrounding wall. In an embodiment the resealable nozzle has a cap to allow a user to cover the resealable nozzle. In an embodiment the nozzle cap has a threaded surrounding wall that mates with the threaded wall surrounding the resealable nozzle.

In an embodiment the resealable nozzle has a tapered surrounding wall. In an embodiment the resealable nozzle has a cap to allow a user to cover the resealable nozzle. In an embodiment the nozzle cap has a tapered surrounding wall that mates with the tapered wall surrounding the resealable nozzle.

In an embodiment, the collection container is a syringe with a luer lock style connector surrounding the resealable nozzle, and a nozzle cap with a luer lock style female mate to the luer lock style connector surrounding the resealable nozzle.

In an embodiment, a plunger can be inserted through the inlet baffle and used to propel the contents (such as, for example, the sample dose and solvent) through the nozzle.

In an embodiment, the collection container has an interior filter held in place with a filter lock ring and a filter support. In an embodiment, the filter is positioned in the lower interior of the collection container. In an embodiment the filter is positioned in the interior of the collection container closer to the flange end. The filter support keeps the filter sitting parallel to the inlet baffle opening and the filter lock ring holds the filter in place on top of the filter support.

In an embodiment, various elements of the sampling apparatus, such as the collection container, filter lock ring, filter support, inlet baffle, and nozzle are made as a single three-dimensionally printed component. In an embodiment, one or more than one of various elements of the sampling apparatus, such as the collection container, filter lock ring, filter support, inlet baffle, and nozzle are made as separate three-dimensionally printed components. In an embodiment, one or more than one of various elements of the sampling apparatus, such as the collection container, filter lock ring, filter support, inlet baffle, and nozzle are made by injection molding.

In an embodiment, the present invention is an apparatus, wherein the apparatus is configured to collect a sample dose from a drug delivery device, wherein the sample dose is an aerosol, wherein the drug delivery device is selected from the group consisting of a metered dose inhaler, a pressurized metered dose inhaler, and a dry powder inhaler, and wherein the apparatus comprises:

a. a collection assembly, wherein the collection assembly comprises:
  i. a collection container, wherein the collection container comprises a hollow cylinder having an inner surface and an outer surface with a flange end having a first opening operatively connected to the hollow cylinder, and a nozzle end having a second opening operatively connected to the hollow cylinder opposite the flange end, wherein the nozzle end is configured to allow the collection container to connect to a system configured to apply negative pressure through the nozzle;
  ii. a closure assembly, comprising a resealable inlet baffle and an inlet baffle cap, wherein the inlet baffle is configured to operatively connect to the flange end of the collection container, and accept and form a seal with a mouthpiece of the drug delivery device;
  iii. a filter, wherein the filter is situated inside the hollow cylinder, wherein the filter is supported by a filter support, wherein the filter is held in place by the filter support and a filter ring, wherein the filter support or the filter ring or both the filter support and filter ring contact the inner surface of the hollow cylinder, wherein the filter is configured to allow gas to flow through the filter, and trap the sample dose; and
  iv. a resealable nozzle;
  v. a nozzle cap, wherein the nozzle cap is configured to seal the nozzle end of the collection container; and
b. a removable plunger, wherein the plunger is configured to pass through the inlet baffle into the collection container and contact the inner surface of the collection container.

In an embodiment, the apparatus further comprises a sensor that is configured to do one, or more than one of the following activities selected from the group consisting of:

a. ensuring that the apparatus is in place in a system prior to actuation of an MDI or pMDI or DPI device;
b. storing and transmitting information that identifies the manufacturer of the apparatus;
c. storing and transmitting information that identifies and/or limits the number of times the apparatus may be used;
d. storing and transmitting information that identifies the sample that is to be contained within the apparatus; and
e. storing and transmitting other information including, but not limited to, patient data, time and/or date of use of the apparatus, and the like.

In an embodiment, the sensor is configured to communicate with an external system. In an embodiment, the external system can modify the information stored in the sensor.

In an embodiment, the filter support is a mesh. In an embodiment, the filter is glass fiber. In an embodiment, the filter has an aerosol retention of 0.3 μm. In an embodiment, the filter is configured to collect a sample dose at flow rates up to 100 1/min.

In an embodiment, the inlet baffle is configured to:
a. operatively connect to the flange end of the collection container via a connection assembly; and
b. accept and form a seal with a mouthpiece of the drug delivery device, wherein the connection assembly comprises an inlet locking ring into which the collection container is inserted through, wherein the inlet locking ring is configured to lockingly engage with the inlet ring and the flange end of the collection container, wherein the flange end of the collection chamber is configured to lockingly engage with the inlet locking ring and the inlet ring, and wherein the inlet ring of the connection assembly is configured to lockingly engage with the inlet locking ring.

In an embodiment, the present invention is a method for collecting a sample dose of the contents of a drug delivery device, using an embodiment of the apparatus of the present invention, comprising:

a. removing an inlet baffle cap from a resealable inlet baffle positioned on a collection container;
b. connecting the nozzle end of the collection container to a negative pressure source;
c. preparing a drug delivery device for actuation and inserting the drug delivery device in the inlet baffle;
d. actuating the drug delivery device and then removing the drug delivery device from the inlet baffle;
e. removing the apparatus from the negative pressure and placing the nozzle cap on the resealable nozzle end of the collection container, thereby sealing the nozzle end;
f. introducing solvent into the collection chamber and sealing the inlet baffle with the inlet baffle cap;
g. agitating the apparatus, then removing the inlet baffle cap from the resealable inlet baffle, then inserting a plunger into the collection container;
h. inverting or appropriately positioning the collection container to prevent spillage and then removing the nozzle cap; and
i. purging air from the collection container, then pushing the plunger fully into the collection container to force the sample dose distributed within the solvent out of the collection container through the nozzle end, and into another container.

In an embodiment, the present invention is a method for collecting a sample dose of the contents of a drug delivery device, using an embodiment of the apparatus of the present invention, comprising:

a. removing an inlet baffle cap from a resealable inlet baffle positioned on a collection container;
b. connecting the nozzle end of the collection container to a negative pressure source;
c. preparing a drug delivery device for actuation and inserting the drug delivery device in the inlet baffle;
d. actuating the drug delivery device and then removing the drug delivery device from the inlet baffle;
e. removing the apparatus from the negative pressure and placing the nozzle cap on the resealable nozzle end of the collection container, thereby sealing the nozzle end;
f. introducing solvent into the collection chamber and sealing the inlet baffle with the inlet baffle cap;
g. agitating the apparatus, then removing the nozzle cap;
h. connecting the nozzle end of the collection container to a negative pressure source; and
i. removing the sample dose distributed within the solvent out of the collection container through the nozzle end, and into another container.

In an embodiment, the sample dose is removed from the apparatus for testing. In an embodiment, the sample dose is removed from the apparatus and disposed of. In an embodiment, a single sample dose is collected. In an embodiment, more than one sample dose is collected.

BRIEF DESCRIPTION OF THE DRAWINGS

FIGS. 3A-12 show an embodiment of a method of testing a drug delivery device (such as a MDI or pMDI or DPI) using a sampling apparatus of the present invention.

FIG. 3A shows an embodiment of a sampling apparatus of the present invention at the beginning of a method of testing a drug delivery device that includes a closure assembly having a resealable inlet baffle and an inlet baffle cap on the inlet baffle, which is attached to the inlet baffle with a connector; a collection container that is a syringe; a filter positioned in the interior of the collection container (not visible); and a nozzle. The nozzle cap has been removed from the resealable nozzle.

FIG. 3B shows the removal of the inlet baffle cap from the resealable inlet baffle and a connector to a negative pressure source such as a vacuum being attached to the nozzle.

FIGS. 4A and 4B show the insertion of a drug delivery device into the inlet baffle followed by actuation of the drug delivery device.

FIGS. 6A and 6B show that after disconnecting the connector to the negative pressure source from the resealable nozzle, the user places the nozzle cap on the nozzle.

FIGS. 7A-7C show a liquid solvent being introduced into the collection container through the inlet baffle and then the capping of the inlet baffle with the inlet baffle cap.

FIG. 11 shows the plunger being pushed into the collection container to force out through the nozzle any air that may be present in the collection container.

FIG. 12 shows the continual pushing of the plunger into the collection container to force the agitated solvent containing the sample dose from the collection container into another container in which the sample dose will be tested and/or analyzed.

FIGS. 13A-13G show an embodiment of a closure assembly of a sampling apparatus of the present invention having a slotted opening and an inlet baffle cap that snaps on to the resealable inlet baffle and is connected to the inlet baffle by a connector.

FIGS. 14A-14G show an embodiment of a closure assembly of a sampling apparatus of the present invention and an inlet baffle cap that snaps on to the resealable inlet baffle and is connected to the inlet baffle by a connector.

FIGS. 15A-15G show an embodiment of a resealable inlet baffle of a sampling apparatus of the present invention having a slotted opening and an inlet baffle cap that snaps on to the inlet baffle and is connected to the inlet baffle by a connector.

FIGS. 16A-16G show an embodiment of a closure assembly of a sampling apparatus of the present invention having a slotted opening and an inlet baffle cap that snaps on to the resealable inlet baffle and is connected to the inlet baffle by a connector.

FIG. 22 shows an embodiment of a sampling apparatus and an embodiment of a holder of a sampling apparatus.

Figure 1:
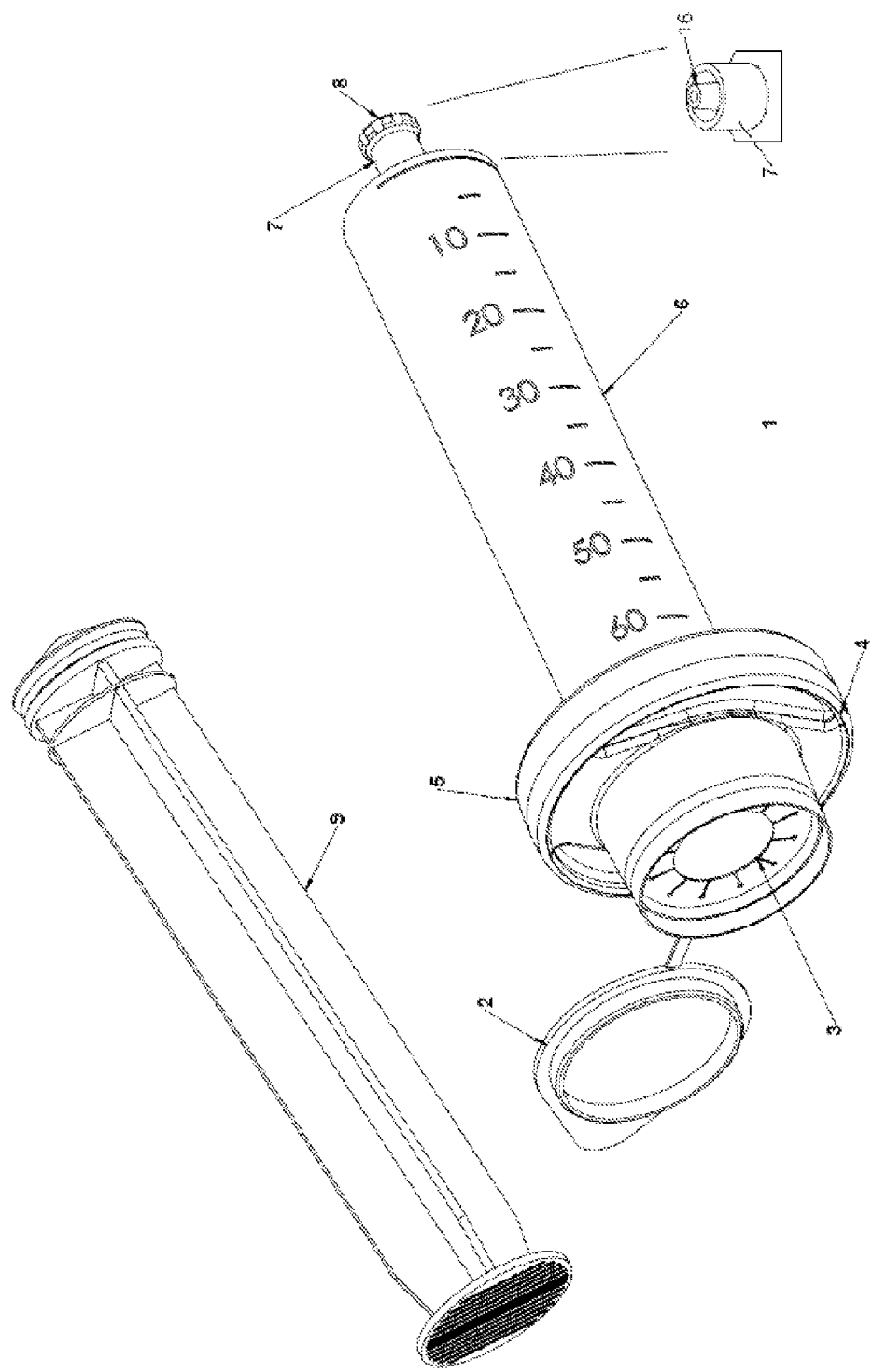
FIG. 1 is an isometric view of components of an embodiment of a sampling apparatus of the present invention.

Among those benefits and improvements that have been disclosed, other objects and advantages of this invention will become apparent from the following description taken in conjunction with the accompanying drawings. The drawings constitute a part of this specification and include exemplary embodiments of the present invention and illustrate various embodiments and features thereof.

DETAILED DESCRIPTION

The present invention relates to a sampling apparatus used for determining the amount and uniformity of the delivered dose emitted by metered-dose inhalers (MDIs) and pressurized metered dose inhalers (pMDIs) and dry powder inhalers (DPIs). In an embodiment, the amount and uniformity of the delivered dose is determined in a sample collected by actuating/firing the drug delivery device into a container containing a filter and connected to a negative pressure source during testing to broadly simulate inhalation. The sample dose is captured, the active drug is dissolved in solvent, an aliquot of the solution is collected and is then analyzed by a suitable method, such as, for example, High Pressure Liquid Chromatography (HPLC) or ultraviolet (UV) spectrophotometric techniques tailored to the specifics of the drug. The choice of technique to analyze the sample dose depends on many factors, such as, for example, the size of the sample dose, the type of drug in the sample dose, the solvent used to collect the sample dose, and the like. The choice of technique is readily selected by one of ordinary skill in the art. In an embodiment, the sampling apparatus is configured to be inserted into, or used in conjunction with an external system that is configured to actuate the drug delivery device and collect the aerosol sample in the apparatus.

In an embodiment, the apparatus is configured to be connected to an external system. In an embodiment, the external system is configured to actuate the drug delivery device. In an embodiment, the external system is configured to process the sample dose. In an embodiment, the external system is configured to actuate the drug delivery device and process the sample dose.

As used herein, the term "delivered dose" or "emitted dose" or "sample dose" or "aerosol sample" refers to the total amount of drug emitted from a drug delivery device (e.g., MDI or pMDI or DPI) and available to the user when the drug delivery device is actuated.

In an embodiment, the present invention is an apparatus, wherein the apparatus is configured to collect a sample dose from a drug delivery device, wherein the sample dose is an aerosol, wherein the drug delivery device is selected from the group consisting of a metered dose inhaler, a pressurized metered dose inhaler, and a dry powder inhaler, and wherein the apparatus comprises:

a. a collection assembly, wherein the collection assembly comprises:

i. a collection container, wherein the collection container comprises a hollow cylinder having an inner surface and an outer surface with a flange end having a first opening operatively connected to the hollow cylinder, and a nozzle end having a second opening operatively connected to the hollow cylinder opposite the flange end, wherein the nozzle end is configured to allow the collection container to connect to a system configured to apply negative pressure through the nozzle;

ii. a closure assembly, comprising a resealable inlet baffle and an inlet baffle cap, wherein the inlet baffle is configured to operatively connect to the flange end of the collection container, and accept and form a seal with a mouthpiece of the drug delivery device;

iii. a filter, wherein the filter is situated inside the hollow cylinder, wherein the filter is supported by a filter support, wherein the filter is held in place by the filter support and a filter ring, wherein the filter support or the filter ring or both the filter support and filter ring contact the inner surface of the hollow cylinder, wherein the filter is configured to allow gas to flow through the filter, and trap the sample dose;

iv. a resealable nozzle; and v. a nozzle cap, wherein the nozzle cap is configured to seal the nozzle end of the collection container; and b. a removable plunger, wherein the plunger is configured to pass through the inlet baffle into the collection container and contact the inner surface of the collection container.

In an embodiment, the apparatus is disposable. In an embodiment, one, or more than one component of the apparatus is disposable. In an embodiment, the collection assembly is disposable. In an embodiment, the closure assembly is disposable. In an embodiment, the filter is disposable. In an embodiment, the nozzle cap is disposable. In an embodiment, the removable plunger is disposable.

As used herein, the term "operatively connected" refers to a connection between two objects that allows the objects to perform the designated function of allowing a substance to pass through an orifice. As a non-limiting example, the term "operatively connected" refers to the connections between the components of the embodiment of the apparatus of the present invention shown in FIG. 4B, that are operatively connected to allow the sample dose released from the drug delivery device 14 to be capable of entering the collection container via the opening 15 in the inlet baffle 3, and to be removed from the collection container through the nozzle end.

Figure 2:
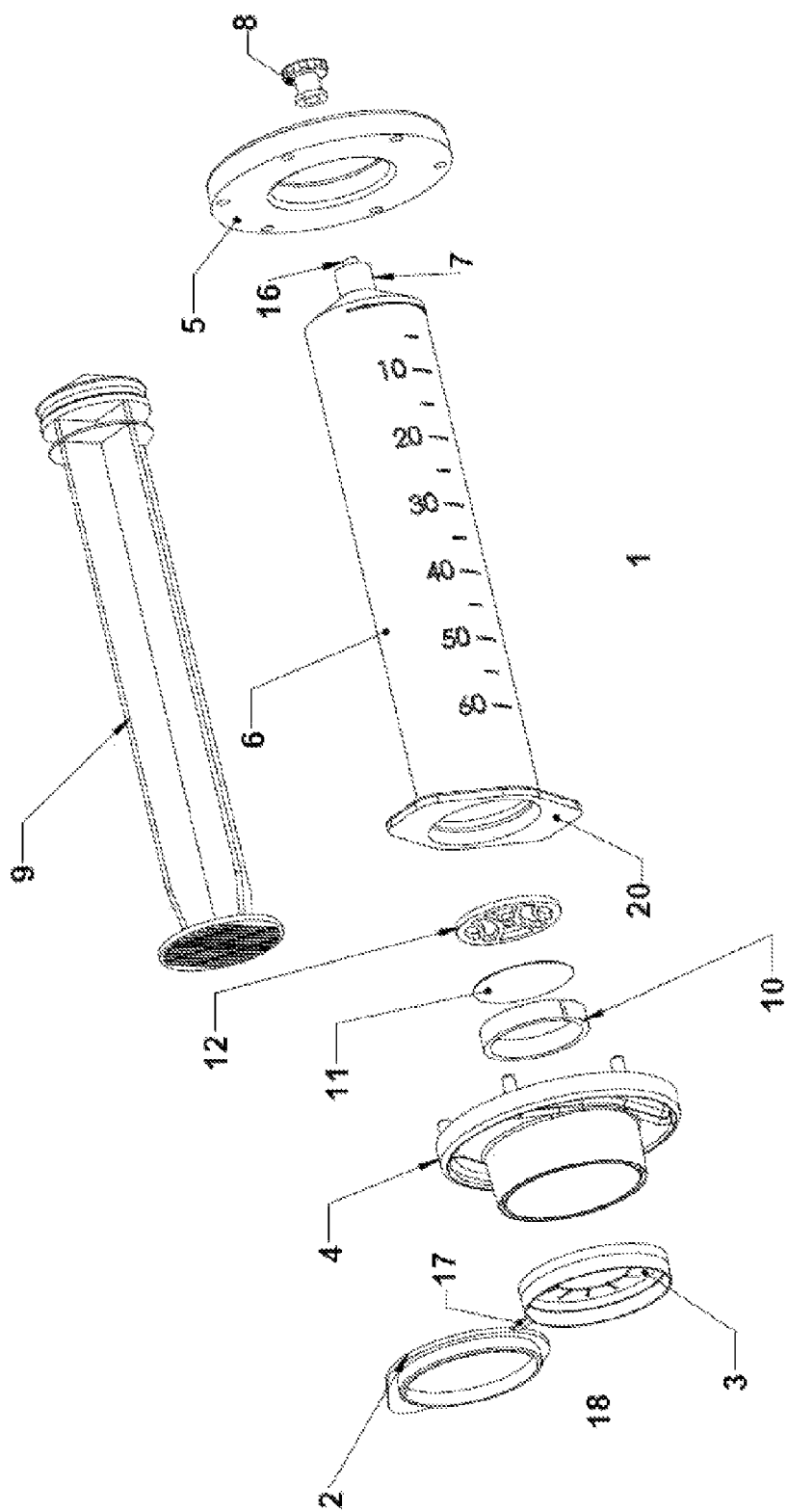
FIG. 2 is an exploded isometric view of the sampling apparatus of FIG. 1.

Referring now to the drawings wherein the references designate identical or corresponding parts throughout the several views, and more particularly to FIG. 1 and FIG. 2 wherein an embodiment of a sampling apparatus 1 of the present invention is illustrated. The sampling apparatus 1 includes a collection container 6. In an embodiment, the collection container 6 is a syringe with an outer and an inner surface that are cylindrically shaped, a resealable nozzle 16 (the "nozzle end"), and two flat opposing, protruding flanges 20 at the end of the syringe opposite to the nozzle (the "flange end"). One of ordinary skill in the art can readily appreciate that the protruding flanges 20 can be of any geometric shape and number.

In an embodiment, the collection container is made from an inert material (i.e., the material does not react with the sample dose and/or the solvent). In an embodiment, the collection container 6 is plastic. In an embodiment, the collection container 6 is polypropylene. In an embodiment, the collection container 6 is glass.

In one embodiment, the flange end of the collection container 6 has a closure assembly 18 made up of a resealable inlet baffle 3 and an inlet baffle cap 2, which are connected by a connector 17. In an embodiment, a resealable inlet baffle 3 is not connected to an inlet baffle cap by a connector. In an embodiment, the inlet baffle 3 is sufficiently designed to accept the mouthpiece of variously sized and shaped MDI or pMDI or DPI devices. In an embodiment, the inlet baffle 3 is sufficiently designed to accept a plunger 9. In an embodiment, the plunger 9 is inserted through the opening in inlet baffle 3 and used to propel the contents (such as, for example, the sample dose and solvent) through the nozzle 16. In an embodiment, rather than two flat opposing, protruding flanges 20, the end of the collection container opposite the nozzle end is sufficiently shaped and sized to allow the affixation of an inlet baffle to the collection container 6. In an embodiment, rather than two flat opposing protruding flanges 20, the end of the collection container opposite the nozzle end has a rim flange around the outer circumference of the collection container.

In an embodiment, the inlet baffle 3 is affixed to an inlet ring 4. In an embodiment, the inlet baffle 3 is integral to the closure assembly and is affixed to an inlet ring 4 that sits on the top side of the flanges 20 and secures the inlet baffle 3 to the collection container 6 by means of an inlet locking ring 5. In an embodiment the inlet ring 4 secures to the inlet locking ring 5 by means of male protrusions from the underside of the inlet ring 4 snapping into mating female intrusions on the upper side of inlet locking ring 5. The inlet baffle 3/inner ring 4 is sufficiently designed to form a seal between the container 6 and the mouthpiece of an MDI/pMDI/DPI mouthpiece. In an embodiment, the closure assembly is configured to affix to the inlet ring 4.

In an embodiment, the inlet baffle is configured to:

a. operatively connect to the flange end of the collection container via a connection assembly; and b. accept and form a seal with a mouthpiece of the drug delivery device, wherein the connection assembly comprises an inlet locking ring into which the collection container is inserted through, wherein the inlet locking ring is configured to lockingly engage with the inlet ring and the flange end of the collection container, wherein the flange end of the collection chamber is configured to lockingly engage with the inlet locking ring and the inlet ring, and wherein the inlet ring of the connection assembly is configured to lockingly engage with the inlet locking ring.

As used herein, the term "connection assembly" refers to the inlet ring 4 and the inlet locking ring 5.

The inlet baffle cap 2 allows a user to cover the resealable inlet baffle 3. In an embodiment of the present invention, the cap 2 is attached to the inlet baffle 3 by means of a connector 17. The closure assembly 18 will be described in more detail with respect to FIGS. 13, 14, 15, and 16.

As used herein, the term "closure assembly" refers to the inlet baffle 3 and the inlet baffle cap 2. In an embodiment, the inlet baffle 3 and the inlet baffle cap 2 are connected by a connector 17.

In an embodiment of the invention, the collection container 6 has a resealable nozzle 16 with a threaded surrounding wall 7. In an embodiment, the threaded surrounding wall 7 is a luer lock style connector. The resealable nozzle 16 has a nozzle cap 8 that, in an embodiment of the invention, has a threaded cavity that mates with the threaded wall 7 surrounding the nozzle 16. In an embodiment, the nozzle cap 8 is the female mate to the luer lock style connector.

In an embodiment of the invention, the collection container 6 has a nozzle with a tapered wall surrounding the nozzle. In an embodiment, the resealable nozzle has a nozzle cap that has a tapered surrounding wall that mates with the tapered wall surrounding the nozzle.

In an embodiment of the invention, the collection container 6 has an interior filter 11 sitting parallel to the opening of the inlet baffle 3 and held in place with a filter lock ring 10 on the inlet baffle 3 side of the filter 11 and a filter support 12 on the nozzle end 16 of the collection container 6 and on which the filter 11 sits. In an embodiment, the filter system 10, 11, 12 is positioned in the interior of the collection container 6 close to the nozzle end. In an embodiment, the lock ring 10 is an O-ring.

In an embodiment, the filter complies with the specifications set forth in USP 37 NF 32. The filter may be made from any material suitable for complying with the requirements of USP 37 NF 32, the choice of which is readily determined by one of ordinary skill in the art. In an embodiment, the filter complies with whatever test specifications the user may determine. For example, in an embodiment, the filter is inert and does not react with the drug. In another example, the filter is inert and does not react with the solvent used to prepare the sample for testing. In an embodiment, the filter 11 is a glass fiber filter. In an embodiment, the filter 11 is a 25 mm glass fiber filter having an aerosol retention of 0.3 microns. In an embodiment, the filter 11 is a 25 mm glass fiber filter enabling dosage collection at flow rates up to 100 L/min. In an embodiment, the filter is a material sufficient to retain the sample dose within the collection container while allowing gas to flow through the filter. In an embodiment, the filter has an aerosol retention relative to a retention level sufficient to retain the sample dose of the MDI or pMDI or DPI.

In an embodiment, the filter is configured to collect an aerosol sample at flow rates up to rates sufficient to perform the test desired to be performed with the apparatus.

In an embodiment, the collection container is an inert (relative to the drug and solvents used in the dissolution process) material (e.g., polypropylene or polyethylene plastic).

In an embodiment, the filter is capable of capturing, trapping, or absorbing an aerosol sample corresponding to a single dose of the contents of a drug delivery device. In an embodiment, the filter is capable of capturing, trapping, or absorbing an aerosol sample corresponding to the entire contents of a drug delivery device. In an embodiment, the filter is capable of capturing, trapping, or absorbing an aerosol sample corresponding to 100%, or 90%, or 80%, or 70%, or 60%, or 50%, or 40%, or 30%, or 20%, or 10% of the contents of the drug delivery device.

In an embodiment, the filter degrades or dissolves when solvent is added. In an embodiment, the degradation of the filter aids collection of the aerosol sample that is captured, trapped, or absorbed by the filter. In an embodiment, the filter support 12 is an open-mesh filter support. In an embodiment, the open-mesh filter support is a stainless steel screen. In an embodiment, the open-mesh filter support is plastic. In an embodiment, the filter support 12 is an inert material. In an embodiment, the filter lock ring 10 is an inert material.

In an embodiment, elements of the sampling apparatus, such as the collection container, filter lock ring, filter support, inlet baffle, and nozzle, are made as a single three-dimensionally printed component.

In an embodiment, one or more than one element of the sampling apparatus, such as the collection container, filter lock ring, filter support, inlet baffle, and nozzle, are made as three-dimensionally printed components.

In an embodiment, one or more than one element of the sampling apparatus, such as the collection container, filter lock ring, filter support, inlet baffle, and nozzle, are injected molded.

In an embodiment, the connection assembly contains a sensor 26. The location of the sensor is readily selected by one of ordinary skill in the art. In an embodiment, the sensor 26 is situated in the inlet ring 4. In an embodiment, the sensor 26 is situated in the inlet locking ring 5. In an embodiment, the sensor is situated in the outer wall of the inlet baffle.

In an embodiment, the sensor 26 contains a microchip that is configured to store and transmit information that identifies the manufacturer of the apparatus. In an embodiment, the microchip is further configured to store and transmit information that identifies and/or limits the number of times the apparatus may be used. In an embodiment, the microchip is further configured to store and transmit information that identifies the sample that is to be contained within the apparatus. In further embodiments, other information may be stored and transmitted, including, but not limited to, patient data, time and/or date of use of the apparatus, and the like.

In an embodiment, the sensor 26 is configured to form a data connection with a system that actuates the drug delivery device, and transmits the information stored on the sensor to the system.

In an embodiment, the sensor 26 is configured to form a data connection with a system that actuates the drug delivery device and receives information from the system. In an embodiment, the information received from the system identifies and/or limits the number of times the apparatus may be used. In an embodiment, the information received from the system identifies the sample that is to be contained within the apparatus. In an embodiment, the information received from the system identifies the user of the system. In further embodiments, other information may be transmitted to the sensor 26, including, but not limited to, patient data, time and/or date of use of the apparatus, and the like.

Referring to FIG. 22, in an embodiment, a data connection is formed between a system that actuates the drug delivery device when the connection assembly of apparatus 1 is placed into receptacle 27 that contains a sensor reader 28. In an embodiment, the data connection is formed when the sensor 26 and sensor reader 28 are aligned. In an embodiment, the data connection is formed when the sensor reader 28 detects sensor 26 and, sensor 26 and sensor reader 28 are aligned. In an embodiment, the slot 29 in receptacle 27 is configured to accept apparatus 1 that has been correctly assembled, and to ensure alignment of sensor 26 and sensor reader 28.

In an embodiment, the present invention relates to a method of collecting an aerosol sample dose and preparing it for testing and/or chemical analysis. FIGS. 3A-12 show an embodiment of a method of testing a drug delivery device (such as an MDI or pMDI or DPI) using a sampling apparatus of the present invention. FIG. 3A shows the sampling apparatus of FIG. 1 and FIG. 2 having the inlet baffle assembly 18 including the resealable inlet baffle 3, the connector 17, the inlet baffle cap 2, the collection container 6, the filter 11, the resealable nozzle 16, the nozzle cap 8, and the plunger 9.

In an embodiment, the apparatus is supplied fully assembled except for the plunger 9, which is supplied separately.

As illustrated in FIG. 3B, the inlet baffle cap 2 is removed from the inlet baffle 3 and the nozzle 16 is connected to a negative pressure source, such as a vacuum, via a suitable interface or fitting 13, followed by the negative pressure source being turned to the on position. In an embodiment, in the on position, the negative pressure source has a steady flow rate. In an embodiment, the negative pressure source includes a flow regulator and a flowmeter. The negative pressure source should be capable of pulling air through the complete assembly, including the filter and the sample dose, at the desired flow rate.

As illustrated in FIGS. 4A and 4B, a MDI, pMDI, DPI, or similar device 14, is prepared for actuation and inserted into the inlet baffle 3, via the opening 15. In an embodiment, if a MDI is being tested, the air flow rate from the negative pressure source may be fixed at a rate of 28.3 L/min (±5%) equivalent to 1 cubic foot per minute. In an embodiment, if a MDI is being tested, the air flow rate from the negative pressure source may be fixed at any desirable rate for the user's test purposes.

Figures 5A, 5B:
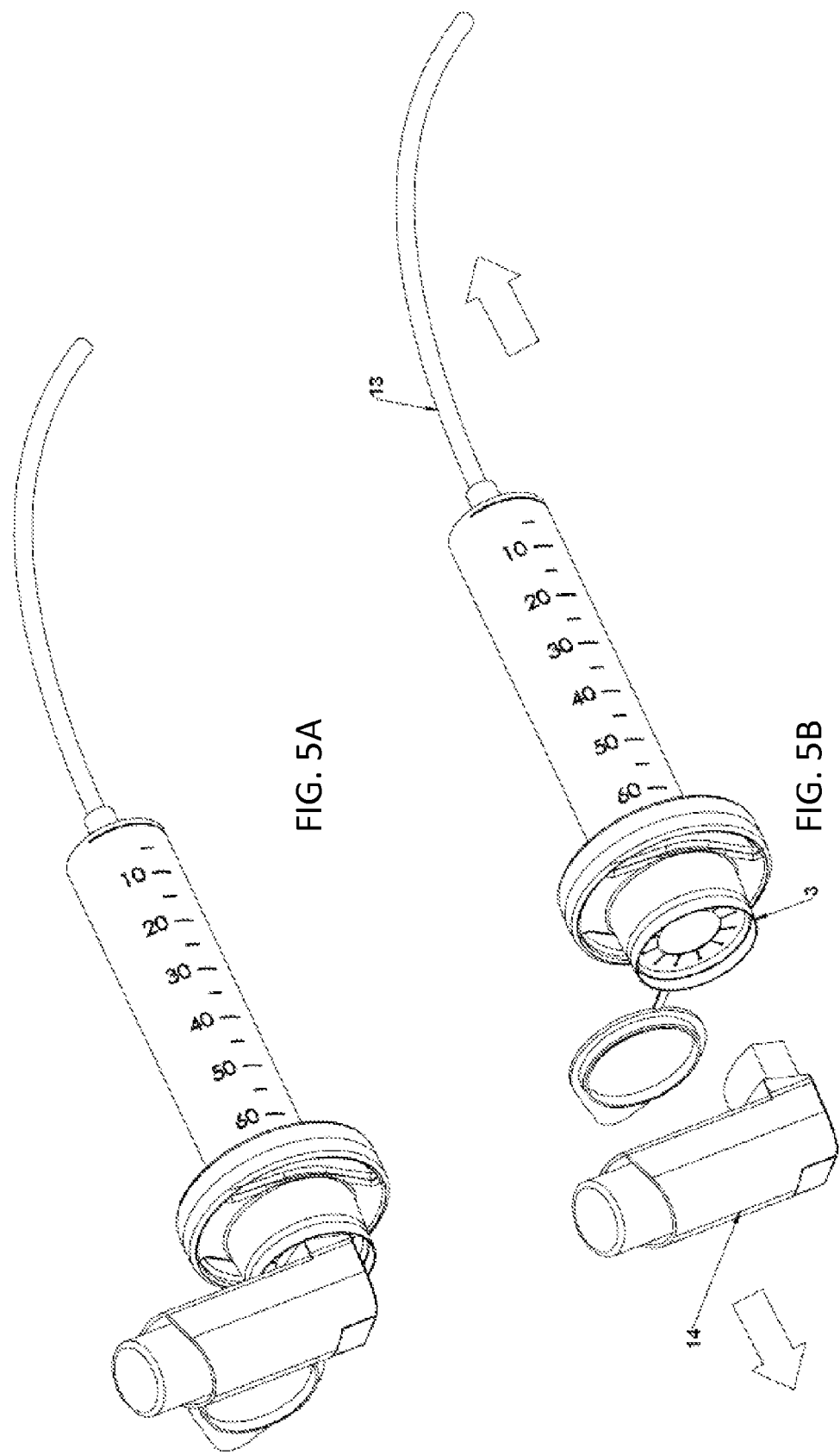
FIGS. 5A and 5B show after actuating the drug delivery device, a user removes the drug delivery device from the inlet baffle and disconnects the connector to the negative pressure source from the nozzle.
Figure 8B:
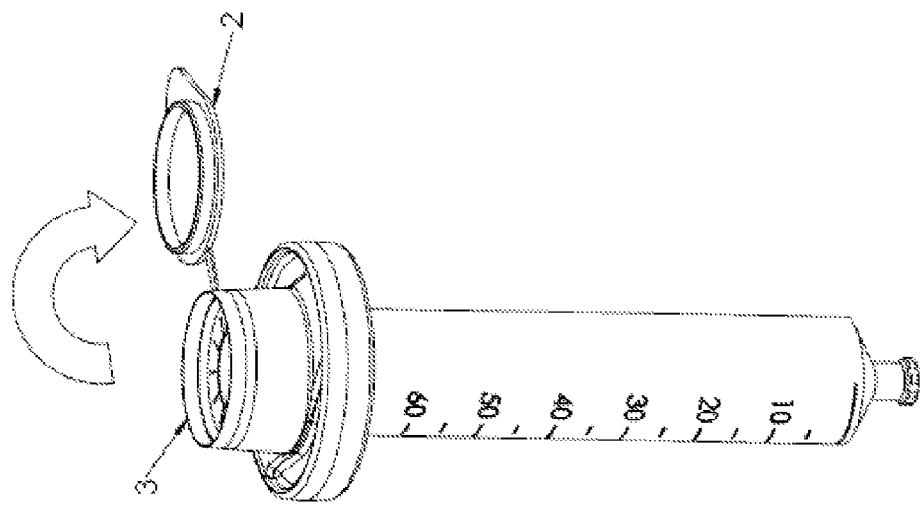
FIGS. 8A and 8B show agitation of the capped sampling apparatus to disperse the sample dose throughout the liquid solvent, and then removal of the inlet baffle cap from the resealable inlet baffle.
Figure 8A:
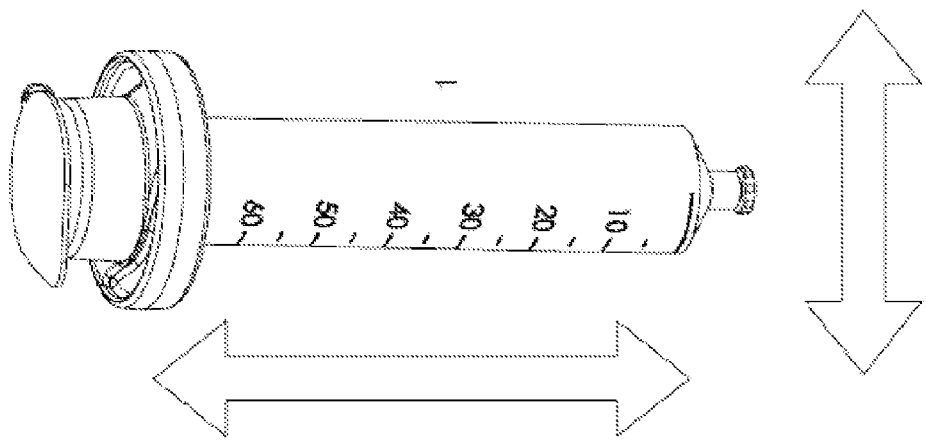
Figure 9B:
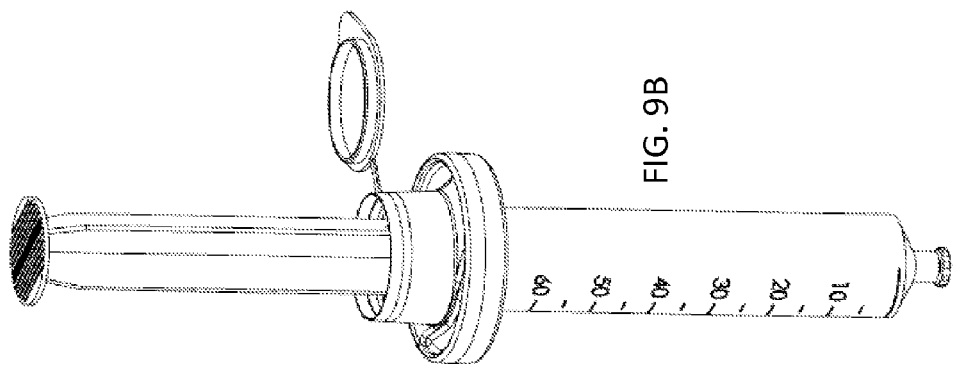
FIGS. 9A and 9B show the introduction of a plunger into the collection container through the inlet baffle.
Figure 9A:
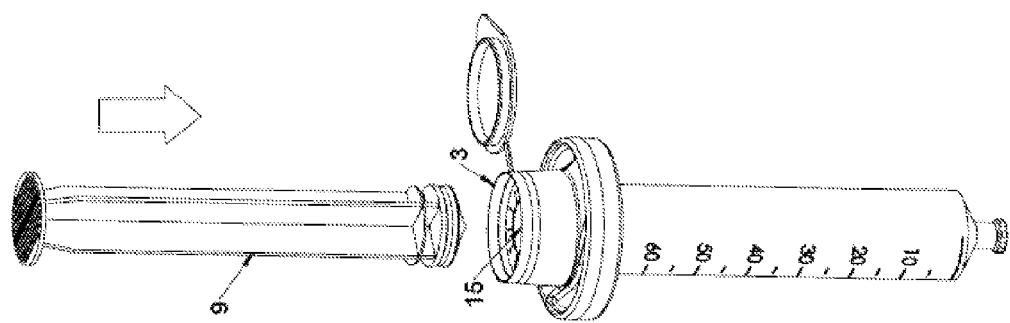
Figure 10B:
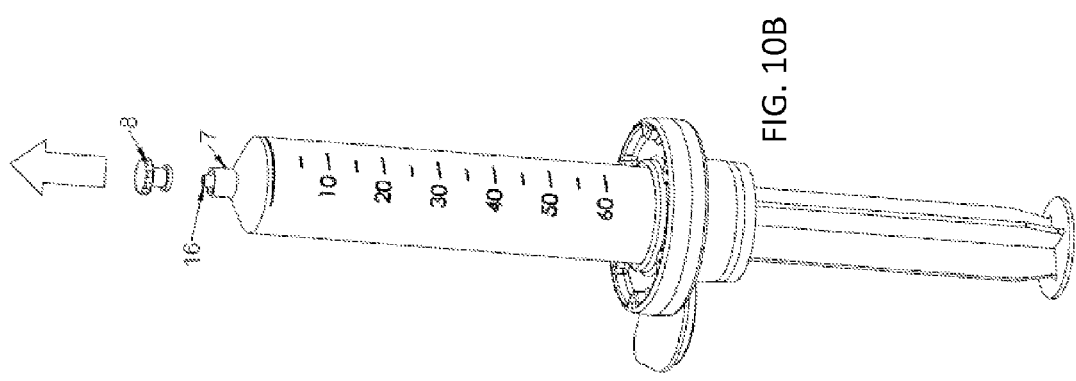
FIGS. 10A and 10B show the inversion of the collection container and removal of the nozzle cap from the resealable nozzle.
Figure 10A:
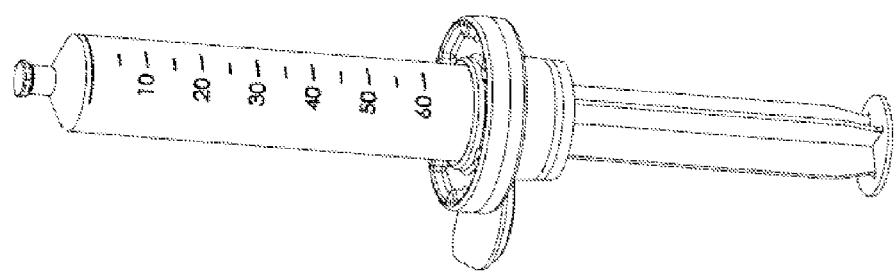
Figure 11:
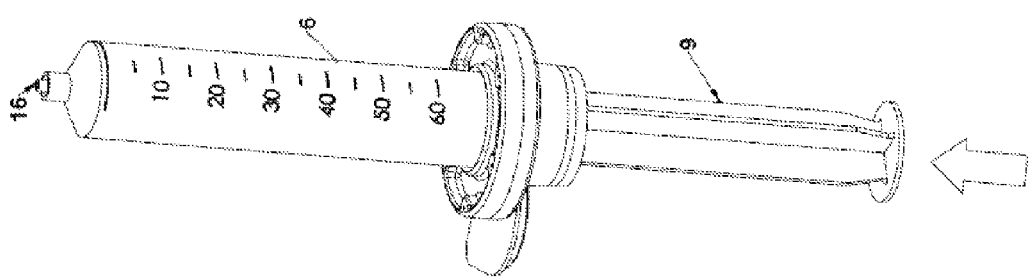
Figure 17:
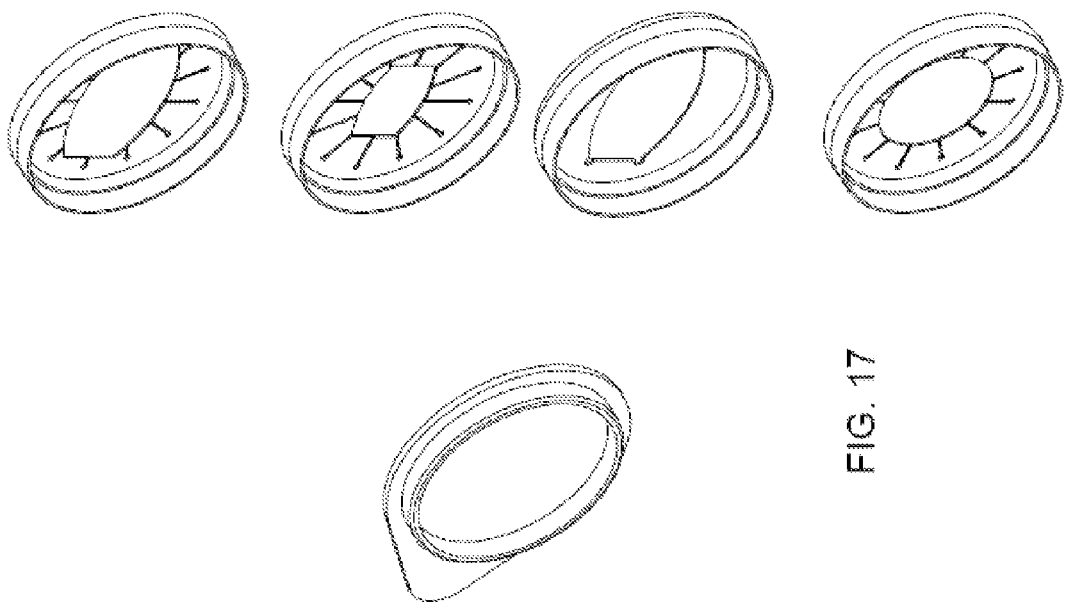
FIG. 17 shows embodiments of closure assemblies of a sampling apparatus of the present invention and an inlet baffle cap that snaps onto a resealable inlet baffle and is not connected to an inlet baffle with a connector.

As illustrated in FIGS. 5A and 5B, the device is actuated into the collection container 6 and then removed from the inlet baffle 3. The negative pressure source is then turned to the off position and the collection container 6 is detached from the negative pressure source. In FIGS. 6A and 6B, the resealable nozzle 16 is covered with the nozzle cap 8 to prevent any of the material collected from exiting the container 6. As illustrated in FIGS. 7A, 7B and 7C, solvent is added to the collection container 6 by inserting it through the inlet baffle 3, via the opening 15. The inlet baffle cap 2 is placed over the resealable inlet baffle 3 to prevent any of the material collected from exiting the flange end of the collection container 6. In FIGS. 8A and 8B, the collection container 6 is agitated as appropriate to allow the sample dose emitted from the device into the collection container 6 to be lifted from the filter 11 and the interior surfaces of the apparatus, and dissolved by the solvent. In an embodiment, agitation is done by a rotary mixer that exposes all interior surfaces of the collection container 6 to the solvent and mixes it until uniformly distributed. In an embodiment, agitation is done by a vortex mixer. In an embodiment, agitation is done by sonication. In an embodiment, agitation is done by hand. It is understood that the agitation required is dependent on the material being tested and is subject to frequent changes in method and duration. As illustrated in FIGS. 9A and 9B, the inlet baffle cap 2 is removed from the top of the resealable inlet baffle 3 and an appropriate plunger 9 is inserted into the collection container 6, via the opening 15. The term "appropriate plunger" means a plunger with a size and shape that when inserted into the collection container 6 effectively seals the collection container 6 at the flange end to prevent any of the material collected from exiting the collection container 6 through the inlet baffle 3. In addition, the term "appropriate plunger" means a plunger with a size and shape that when inserted into the collection container pushes substantially all material stuck to the inner surface of the collection container toward the nozzle end. As illustrated in FIGS. 10A and 10B, the collection container 6 is inverted or appropriately positioned to prevent spillage and the nozzle cap 8 is removed. In FIG. 11, air is purged from the collection container 6 by pushing the plunger 9 further into the collection container 6, and then, when any air has been forced out of the collection container 6 the plunger 9 is pushed fully into the collection container 6 to force the sample dose distributed within the solvent out of the collection container 6 and into another container 19, such as a vial, for further testing, such as chemical analysis (see FIG. 12). All components of the present invention may then be discarded as appropriate.

FIGS. 13, 14, 15, and 16 show embodiments of closure assemblies of the present invention. FIGS. 17 and 18 show embodiments of resealable inlet baffles and inlet baffle caps. An acceptable plunger and the mouthpiece of an aerosol drug device such as a MDI, a pMDI, a DPI, or a similar device, may be inserted into the opening. The cap is either releasably or permanently connected to the frame assembly by a connector. In an embodiment shown, the inlet baffle is sized for the inlet baffle cap to snap on with the interior of the inlet baffle wall to the exterior of the resealable inlet baffle. In another embodiment the inlet baffle is sized for the inlet baffle cap to snap on with the exterior of the inlet baffle wall to the interior of the resealable inlet baffle. In another embodiment, the cap is not connected by a connector to the outer wall of the inlet baffle/frame assembly. In another embodiment, the cap screws on to the frame assembly. The connector, inlet baffle, and inlet baffle cap may each be formed of a resilient and flexible material.

FIGS. 13A-13G show an embodiment of a closure assembly of a sampling apparatus of the present invention. In this embodiment, twelve resilient finger members are spaced about an inner periphery of the main body portion and extend radially inwardly to a central opening having a circular shape. Twelve spaces or slots are respectively defined between the adjacent finger members, with each of the finger members and spaces having substantially the same shape and dimensions. Alternatively, the shape and number of the finger members and the slots could be varied. The edges of the respective finger members together define the central opening, which preferably has a minimum diameter $D_1$ that is substantially sized to accept various sizes and shapes of a plunger or a mouthpiece of an aerosol drug delivery device such as a MDI, a pMDI, a DPI, or a similar device.

FIGS. 14A-14G show an embodiment of a closure assembly of a sampling apparatus of the present invention having an inlet baffle with a central single opening.

FIGS. 15A-15G show an embodiment of a closure assembly of a sampling apparatus of the present invention having a slotted opening. In this embodiment, twelve resilient finger members are spaced about an inner periphery of the main body portion and extend radially inwardly to a central opening having a non-circular shape. Twelve spaces or slots are respectively defined between the adjacent finger members, with each of the finger members and spaces having substantially the same shape and dimensions. Alternatively, the shape and number of the finger members and the slots could be varied. The edges of the respective finger members together define the central opening, which preferably has a minimum diameter $D_1$ that is substantially sized to accept various sizes and shapes of a plunger or a mouthpiece of an aerosol drug device such as a MDI, a pMDI, a DPI, or a similar device.

FIGS. 16A-16G show an embodiment of an inlet baffle assembly of a sampling apparatus of the present invention having a slotted opening. In this embodiment of the inlet baffle, twelve resilient finger members are spaced about an inner periphery of the main body portion and extend radially inwardly to a central opening having a non-circular shape. Twelve spaces or slots are respectively defined between the adjacent finger members, with each of the linger members and spaces having substantially the same shape and dimensions. Alternatively, the shape and number of the finger members and the slots could be varied. The edges of the respective finger members together define the central opening, which preferably has a minimum diameter $D_1$ that is substantially sized to accept various sizes and shapes of a plunger or a mouthpiece of an aerosol drug device such as an MDI, a pMDI, a DPI, or a similar device.

FIG. 17 shows an embodiment of the inlet baffle cap that is not connected to a resealable inlet baffle and allows a user to cover the inlet baffle by snapping on an inlet baffle cap. In an embodiment the inlet baffle cap snaps on with the exterior of the inlet baffle to the interior of the inlet baffle cap. In an embodiment the inlet baffle cap snaps on with the interior of the inlet baffle wall to the exterior of the resealable inlet baffle.

Figure 18:
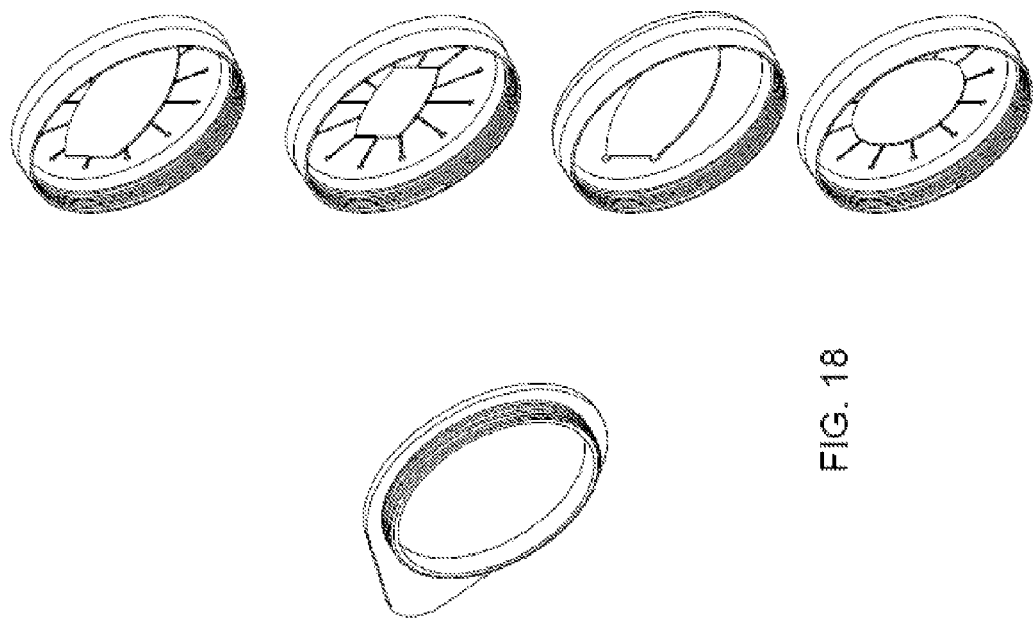
FIG. 18 shows embodiments of closure assemblies of a sampling apparatus of the present invention with a threaded interior wall and an inlet baffle cap with a threaded exterior wall that screws onto an inlet baffle and is not connected to a resealable inlet baffle.

FIG. 18 shows embodiments of inlet baffles that have an interior threaded wall and shows an embodiment of the inlet baffle cap that is not connected to a resealable inlet baffle and has an exterior threaded wall to allow a user to cover the resealable inlet baffle by screwing on an inlet baffle cap. In an embodiment an inlet baffle has an exterior threaded wall and an inlet baffle cap that is not connected to the resealable inlet baffle and has an interior threaded wall to allow a user to cover the inlet baffle by screwing on an inlet baffle cap.

Figure 19:
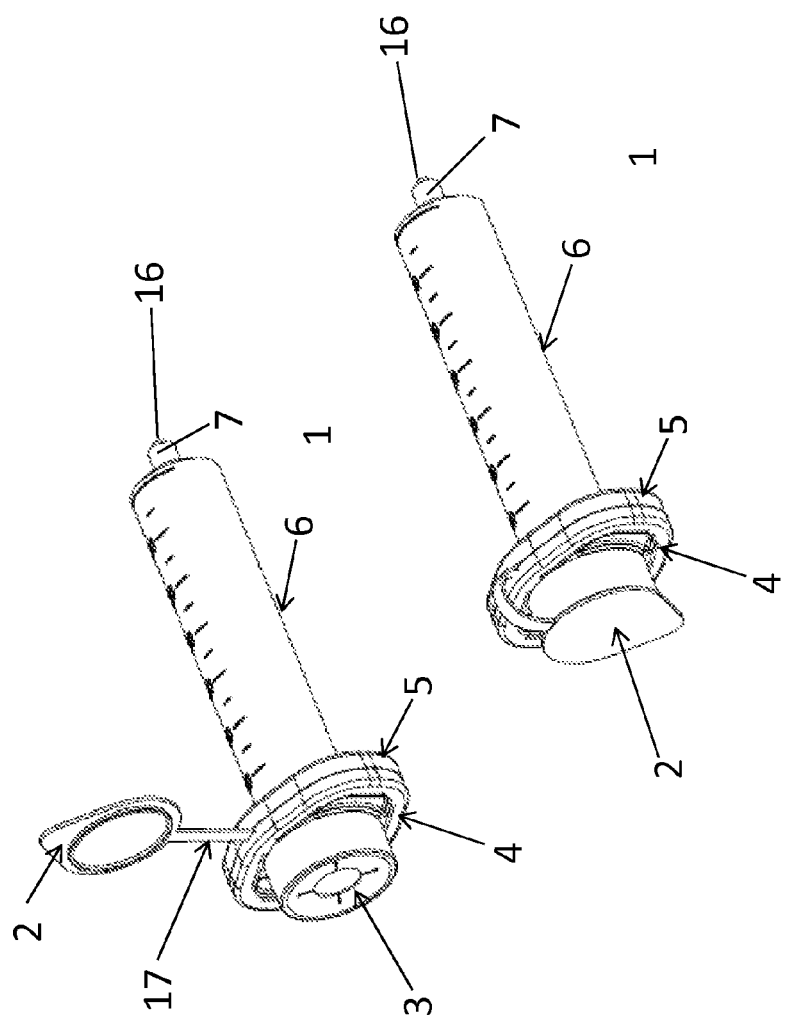
FIG. 19 shows an isometric view of an embodiment of a sampling apparatus of the present invention. The plunger is not shown.
Figure 20:
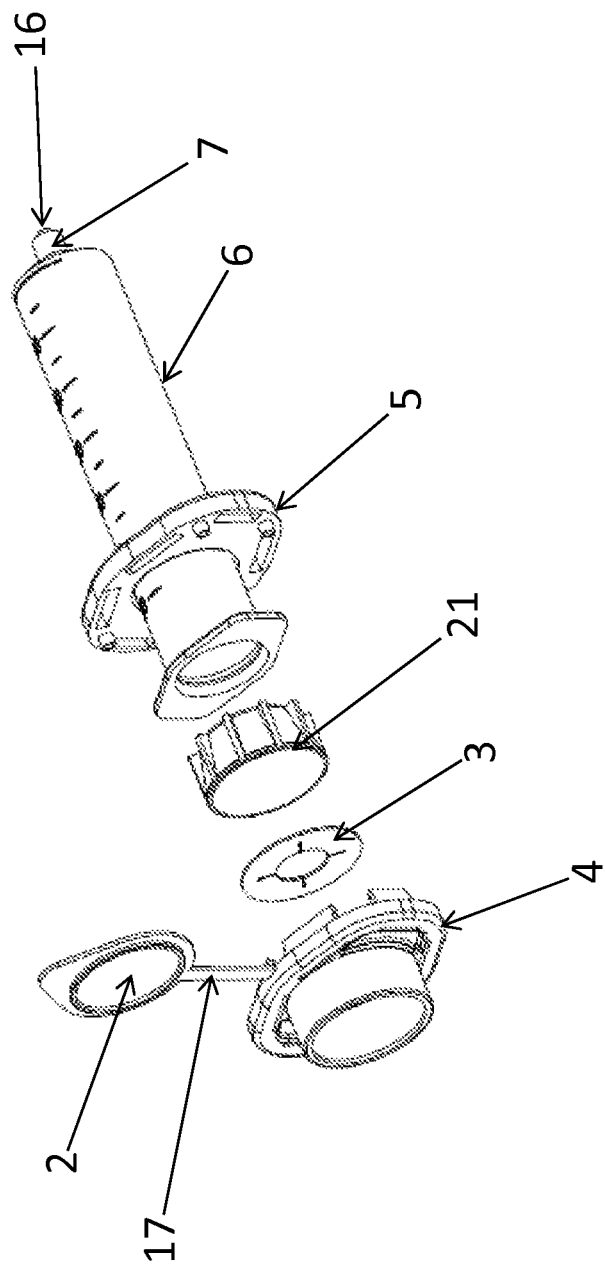
FIG. 20 shows an exploded isometric view of an embodiment of a sampling apparatus of the present invention. The plunger is not shown.
Figure 21:
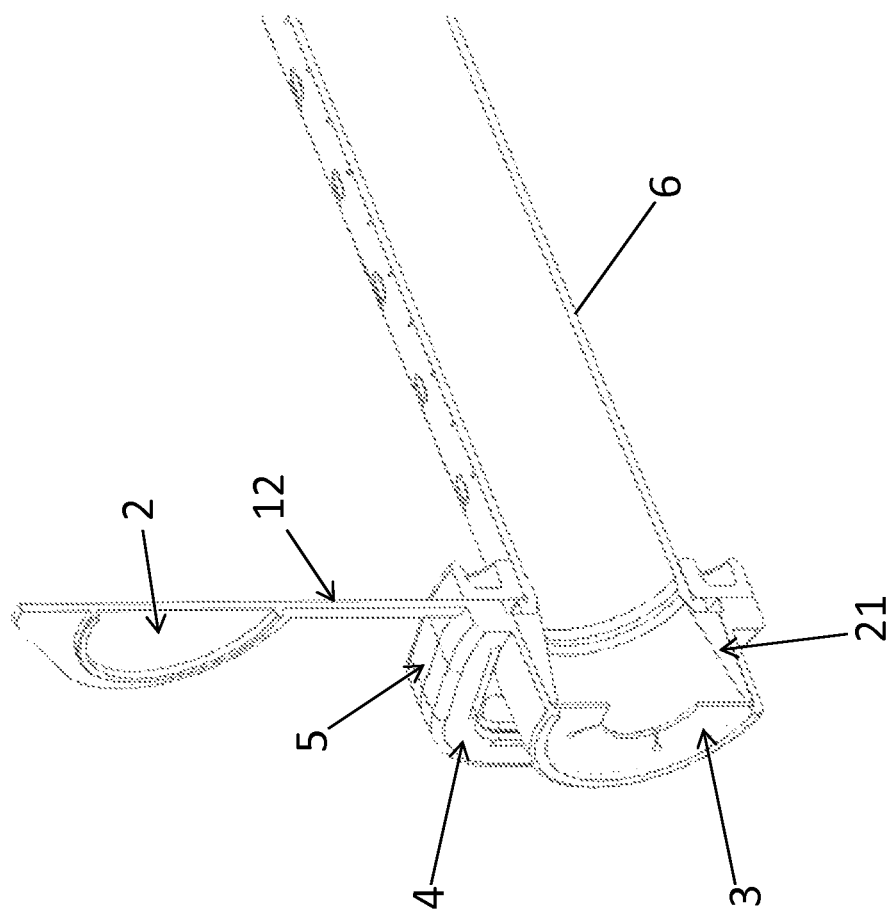
FIG. 21 shows an isometric cross-section view of an embodiment of a sampling apparatus of the present invention. The plunger is not shown.

Referring now to FIGS. 19-21, wherein another embodiment of a sampling apparatus 1 of the present invention is illustrated. The sampling apparatus 1 includes a collection container 6. In an embodiment, the collection container 6 is a syringe with an outer and an inner surface that are cylindrically shaped, a nozzle 16 (the "nozzle end"), and two flat opposing, protruding flanges 20 at the end of the syringe opposite to the nozzle (the "flange end"). In an embodiment, the collection container 6 is plastic. In an embodiment, the collection container 6 is glass. In an embodiment, the collection container is another inert material. The flange end of the collection container 6 has an inlet baffle assembly made up of an inlet baffle 3 connected to an inlet baffle cap 2 by a connector 17. In an embodiment, the inlet baffle 3 is sufficiently designed to accept the mouthpiece of variously sized and shaped MDI, pMDI, DPI, or similar devices. In an embodiment, the inlet baffle 3 is sufficiently designed to accept a plunger 9 (not shown).

In an embodiment, the inlet baffle 3 is held in place inside the inlet ring 4 by a lead-in adapter 21. In an embodiment the inlet ring 4 secures to the inlet locking ring 5 by means of male protrusions 22 from the underside of the inlet ring 4 snapping into mating female intrusions 23 on the upper side of inlet locking ring 5. In an embodiment, inlet ring 4 secures to the inlet ring lock 5 by means of male protrusions 24 from the upper side of the inlet locking ring 5 snapping into mating female intrusions on the lower surface side of inlet ring 4. The inlet baffle 3/inner ring 4 is sufficiently designed to form a seal between the container 6 and the mouthpiece of an MDI, pMDI, DPI, or similar device mouthpiece.

In an embodiment, the mating surfaces of the inlet ring 4 and the inlet locking ring 5 are configured with a recess that matches the shape of the protruding flanges 20.

In an embodiment, the inlet baffle 3 is held in place inside the inlet ring 4 by a lead-in adapter 21. In an embodiment, adapter 21 fits within the opening of the collection container 6 and is configured to hold inlet baffle 3 tightly against the end of the inlet ring 4. An exploded view of an embodiment showing adapter 21 is shown in FIGS. 20 and 21.

In an embodiment, the diameter of the lead-in adapter 21 is larger at the end that contacts the inlet baffle 3, and the diameter tapers inward toward the end of adapter 21 that contacts the collection container 6. In an embodiment, the diameter of the adapter 21 is substantially the same as the diameter of the inner diameter of the collection container 6 so as to allow the adapter 21 to fit tightly into the collection container.

A sampling apparatus of the present invention is sufficiently designed for collecting a sample dose from metered dose inhalers, pressurized metered dose inhalers, dry powder inhalers, and similar devices.

A method of collecting a sample dose and preparing it for testing includes removing an inlet baffle cap from a resealable inlet baffle positioned on a collection container; connecting a nozzle to a negative pressure source, such as a vacuum; turning the negative pressure source to an on position; preparing a MDI, pMDI, DPI, or similar device for actuation and inserting the device into the inlet baffle; actuating the device into the collection container and then removing it from the inlet baffle; turning the negative pressure source to an off position; detaching the collection container from the negative pressure source; covering the resealable nozzle with a nozzle cap to prevent any of the material collected from exiting the container; adding solvent to the collection container by inserting it through the inlet baffle; placing the inlet baffle cap over the inlet baffle to prevent any of the material collected from exiting the flange end of the collection container; agitating the collection container to allow the sample dose emitted from the device into the collection container to be lifted from a filter and the interior surfaces of the collection container, and dissolved by the solvent; removing the cap from the top of the inlet baffle; inserting into the collection container an appropriately sized plunger; inverting, or appropriately positioning to prevent spillage, the collection container and removing the nozzle cap; purging air from the collection container by pushing the plunger further into the collection container, and then, when any air has been forced out of the collection container; pushing the plunger fully into the collection container to force the sample dose distributed within the solvent out of the collection container and into another container.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

What is claimed is:

1. An apparatus,
   wherein the apparatus is configured to collect a sample dose from a drug delivery device,
   wherein the sample dose is an aerosol,
   wherein the drug delivery device is selected from the group consisting of a metered dose inhaler, a pressurized metered dose inhaler, and a dry powder inhaler, and
   wherein the apparatus comprises:
   a. a collection assembly,
      wherein the collection assembly comprises:
      i. a collection container,
         wherein the collection container comprises a hollow cylinder having an inner surface and an outer surface with a flange end having a first opening operatively connected to the hollow cylinder, and a nozzle end having a second opening operatively connected to the hollow cylinder opposite the flange end,
         wherein the nozzle end is configured to allow the collection container to connect to a system configured to apply negative pressure through the nozzle;
      ii. a closure assembly, comprising a resealable inlet baffle and an inlet baffle cap,
         wherein the inlet baffle is configured to operatively connect to the flange end of the collection container, and accept and form a seal with a mouthpiece of the drug delivery device;
iii. a filter,
wherein the filter is situated inside the hollow cylinder,
wherein the filter is supported by a filter support,
wherein the filter is held in place by the filter support and a filter ring,
wherein the filter support or the filter ring or both the filter support and filter ring contact the inner surface of the hollow cylinder,
wherein the filter is configured to allow gas to flow through the filter, and trap the sample dose;
iv. a resealable nozzle; and
v. a nozzle cap,
wherein the nozzle cap is configured to seal the nozzle end of the collection container; and
b. a removable plunger,
wherein the plunger is configured to pass through the inlet baffle into the collection container and contact the inner surface of the collection container.

2. The apparatus of claim 1, wherein the apparatus further comprises a sensor that is configured to do one, or more than one of the following activities selected from the group consisting of:
a. ensuring that the apparatus is in place in a system prior to actuation of the drug delivery device;
b. storing and transmitting information that identifies the manufacturer of the apparatus;
c. storing and transmitting information that identifies and/or limits the number of times the apparatus may be used;
d. storing and transmitting information that identifies the sample that is to be contained within the apparatus; and
e. storing and transmitting other information including, but not limited to, patient data, time and/or date of use of the apparatus.

3. The apparatus of claim 2, wherein the sensor is configured to communicate with an external system.

4. The apparatus of claim 2, wherein the external system can modify the information stored in the sensor.

5. The apparatus of claim 1, wherein the filter support is a mesh.

6. The apparatus of claim 1, wherein the filter is glass fiber.

7. The apparatus of claim 1, wherein the filter has an aerosol retention of 0.3 μm.

8. The apparatus of claim 1, wherein the filter is configured to collect a sample dose at flow rates up to 100 l/min.

9. The apparatus of claim 1, wherein the inlet baffle is configured to:
a. operatively connect to the flange end of the collection container via a connection assembly; and
b. accept and form a seal with a mouthpiece of the drug delivery device,
wherein the connection assembly comprises an inlet locking ring into which the collection container is inserted through,
wherein the inlet locking ring is configured to lockingly engage with an inlet ring and the flange end of the collection container,
wherein the flange end of the collection chamber is configured to lockingly engage with the inlet locking ring and the inlet ring, and
wherein the inlet ring of the connection assembly is configured to lockingly engage with the inlet locking ring.

10. A method for collecting a sample dose of the contents of the drug delivery device,
wherein the method uses the apparatus of claim 1, and comprises:
a. removing the inlet baffle cap from the resealable inlet baffle positioned on the collection container;
b. connecting the nozzle end of the collection container to the negative pressure source;
c. preparing the drug delivery device for actuation and inserting the drug delivery device in the inlet baffle;
d. actuating the drug delivery device and then removing the drug delivery device from the inlet baffle;
e. removing the apparatus from the negative pressure and placing the nozzle cap on the resealable nozzle end of the collection container, thereby sealing the nozzle end;
f. introducing solvent into the collection chamber and sealing the inlet baffle with the inlet baffle cap;
g. agitating the apparatus, then removing the inlet baffle cap from the resealable inlet baffle, then inserting the plunger into the collection container;
h. inverting or appropriately positioning the collection container to prevent spillage and then removing the nozzle cap; and
i. purging air from the collection container, then pushing the plunger fully into the collection container to force the sample dose distributed within the solvent out of the collection container through the nozzle end, and into another container.

11. The method of claim 10, wherein the sample dose is obtained by using the apparatus and then tested.

12. The method of claim 10, wherein the sample dose is obtained by using the apparatus and then disposed of.

13. The method of claim 10, wherein a single sample dose is collected.

14. The method of claim 10, wherein more than one sample dose is collected.

15. A method for collecting a sample dose of the contents of the drug delivery device,
wherein an method uses the apparatus of claim 1, and comprises:
a. removing the inlet baffle cap from a resealable inlet baffle positioned on the collection container;
b. connecting the nozzle end of the collection container to the negative pressure source;
c. preparing the drug delivery device for actuation and inserting the drug delivery device in the inlet baffle;
d. actuating the drug delivery device and then removing the drug delivery device from the inlet baffle;
e. removing the apparatus from the negative pressure and placing the nozzle cap on the resealable nozzle end of the collection container, thereby sealing the nozzle end;
f. introducing solvent into the collection chamber and sealing the inlet baffle with the inlet baffle cap;
g. agitating the apparatus, then removing the nozzle cap;
h. connecting the nozzle end of the collection container to the negative pressure source; and
i. removing the sample dose distributed within the solvent out of the collection container through the nozzle end, and into another container.

16. The method of claim 15, wherein the sample dose is obtained by using the apparatus and then tested.

17. The method of claim 15, wherein the sample dose is obtained by using the apparatus and then disposed of.

18. The method of claim 15, wherein a single sample dose is collected.

19. The method of claim 15, wherein more than one sample dose is collected.

* * * * *